United States Patent
Bansal

(10) Patent No.: US 8,192,742 B2
(45) Date of Patent: *Jun. 5, 2012

(54) METHOD OF INHIBITING COMPLEMENT ACTIVATION WITH HUMAN ANTI-FACTOR C3 ANTIBODIES AND USE THEREOF

(75) Inventor: Rekha Bansal, Twinsburg, OH (US)

(73) Assignee: NovelMed Therapeutics, Cleveland, OH (US)

( * ) Notice: Subject to any disclaimer, the term of this patent is extended or adjusted under 35 U.S.C. 154(b) by 1170 days.

This patent is subject to a terminal disclaimer.

(21) Appl. No.: 11/690,334

(22) Filed: Mar. 23, 2007

(65) Prior Publication Data

US 2008/0233113 A1 Sep. 25, 2008

(51) Int. Cl.
*A61K 39/395* (2006.01)

(52) U.S. Cl. ............... 424/145.1; 424/141.1; 424/130.1

(58) Field of Classification Search .................. None
See application file for complete search history.

(56) References Cited

OTHER PUBLICATIONS

Dilillo et al. (Molecular Immunology 2006, 43:1010-1019).*
Green (JIM 1999 231:11-23).*
Falkenberg (J. Clin. Chem. Clin. Biochem. 1984, 22:867-882).*

* cited by examiner

*Primary Examiner* — Sharon Wen
(74) *Attorney, Agent, or Firm* — Tarolli, Sundheim, Covell & Tummino LLP

(57) ABSTRACT

A method of inhibiting complement activation mediated by C3b inhibitors in a subject includes administering a C3B inhibitor to the subject to inhibit at least one of C3b binding to factors B and properdin, inhibit C3 cleavage, inhibit the activation of neutrophils, monocytes, platelets, and endothelium; or inhibit the formation of C3a, C5a, and MAC.

8 Claims, 3 Drawing Sheets

METHOD OF INHIBITING COMPLEMENT ACTIVATION WITH HUMAN ANTI-FACTOR C3 ANTIBODIES AND USE THEREOF

FIELD OF THE INVENTION

The present invention relates to the method of inhibiting complement activation by way of inhibition of C3b function. The present invention also relates to a method of inhibiting the formation of complement activation products, inhibiting the complement-mediated activation of neutrophils, monocytes, and platelets, and relates to the treatment of various immunological and clinical disorders resulting from complement activation.

BACKGROUND OF THE INVENTION

The complement system, as a series of chemical reactions, within the immune system aids in the removal of pathogens from an organism providing an early acting mechanism for the initiation and activation of inflammatory response to microbial infection and other acute insults. While complement activation provides a valuable first-line defense against potential pathogens, the activities of complement that promote a protective inflammatory response can also represent a potential threat to the host. For example, neutrophils are activated by C3 and C5 proteolytic products, and are indiscriminate in their release of destructive enzymes possibly causing organ damage. Additionally, host cell lysis may result from complement activation causing the deposition of lytic complement components on microbial targets as well as host cells nearby.

There are implications that the complement system contributes to pathogenesis of numerous acute and chronic disease states, including septic shock, capillary leakage following thermal burns myocardial infarction, post cardiopulmonary bypass inflammation, transplant rejection revascularization following stroke, ARDS, reperfusion injury, rheumatoid arthritis, multiple sclerosis, myasthenia gravis, and even Alzheimer's disease. Although for nearly all of these conditions, complement is not the cause, it is one of several factors involved in pathogenesis and could be a significant pathological mechanism that offers an effective point for clinical control. The need for effective complement inhibitory drugs is signified by growing recognition of the importance of complement-mediated tissue injury in a variety of disease states. Despite this, currently there is a complete absence of approved drugs for human use that specifically target and inhibit complement activation.

The complement system can be activated through three distinct pathways: the classical pathway, the lectin pathway, and the alternative pathway. The classical pathway is most often triggered by an antibody bound to a foreign particle (i.e., an antigen), therefore requiring previous exposure to that antigen for the generation of a specific antibody. So, while the classical complement pathway, as part of the acquired immune system, typically requires antibodies for activation, the alternate pathway can be activated by C3 hydrolysis or antigens without the presence of prior exposure to antibodies.

The binding of a specific recognition molecule C1q, to antigen-bound IgG and IgM is the first step in activation of the classical pathway. Upon binding of C1q to an immune complex, autoproteolytic cleavage of C1r is followed by C1r activation of C1s, which then acquires the capacity to cleave C4 and C2. C4 cleaves into two fragments, C4a and C4b, which allows the C4b fragments, to form covalent bonds with adjacent hydroxyl or amino groups and the subsequent generation of C3 convertase (C4b2b) through non-covalent interaction with the C2b fragment of activated C2. C3 convertase (C4b2b) activates C3 leading to generation of the C5 convertase (C4b2b3b) and formation of the membrane attack complex (C5b-9) that can cause lysis. The activated forms of C3 and C4 (C3b and C4b) are covalently deposited on the foreign target surfaces, which are recognized by complement receptors on multiple phagocytes.

For the activation of the complement system by way of the lectin pathway, the first step is also the binding of particular recognition molecules, then followed by the activation of associated serine proteases. The lectin pathway uses a protein similar to C1q of the classical complement pathway, and allows binding on multiple pathogens. However, rather than the binding of immune complexes by C1q, the recognition molecules in the lectin pathway are carbohydrate-binding proteins (mannan-binding lectin MBL, and Ficolins). MBL is a calcium-dependent lectin that can initiate the complement cascade by binding carbohydrates to pathogen surfaces.

During inflammation, the expression of MBL is up regulated and L-ficolin is present in serum at similar concentrations as MBL. Therefore, the L-ficolin arm of the lectin pathway is potentially comparable in strength to the MBL arm. Human MBL forms a specific and high affinity interaction through its collagen-like domain with unique C1r/C1s-like serine proteases, termed MBL-associated serine proteases (MASPs). C3b is the protease responsible for activating C4 and C2 to generate the C3 convertase, C4b2b. The mannan-binding lectin pathway is widely thought to have a role in host defense against infection. It has been noted that such patients display substantial increased susceptibility to recurring infections. Other studies have implicated the classical and alternative pathways in the pathogenesis of ischemia/reperfusion injury and the role of the lectin pathway in this disease remains controversial.

The alternative pathway begins the biochemical cascade by spontaneous activation triggered by foreign or other abnormal surfaces including bacteria, damaged tissue, or virally infected cells. In order for the alternative pathway to function there are four plasma proteins required that are directly involved in the alternative pathway and include C3, factors B and D, and P. Proteolytic cleavage of C3b from native C3 is required for the cascade of the alternative pathway to function. C3 belongs to a family of proteins along with C4 and α-2 macroglobulin, which contain a rare posttranslational modification known as a thio-ester bond. Known as the thioester group, they are composed of a glutamine whose terminal carbonyl group is bound to the sulfhydryl group of a cysteine three amino acids away. The bond created is generally unstable and allows the electrophilic carbonyl group of glutamine to form a covalent bond with other molecules via hydroxyl or amino groups. The thioester bond is reasonably stable when isolated within a hydrophobic pocket of intact C3. However, the proteolytic cleavage of C3 to C3b results in the release of a high energy and therefore highly reactive thioester bond on C3b. This mechanism causes C3b to covalently attach to a target as well as an additional molecule of C3a also is released.

In combination with the acknowledged role of thioester in covalent attachment of C3b to complement targets, the C3 thioester is also thought to have a pivotal role in triggering the alternative pathway. The cascade of the alternative pathway also provides a powerful amplification loop for the lectin and classical pathway C3 convertase (C4b2b) since any C3b generated can participate with factor B in forming additional alternative pathway C3 convertase (C3bBb). This implies that inhibition of C3b function will inhibit all three pathways to complement system activation. The alternative pathway C3 convertase is stabilized by the binding of properdin extending the C3 convertase half-life six to ten fold. Addition of C3b to the C3 convertase leads to the formation of the alternative pathway C5 convertase.

Each of the three pathways (classical, lectin and alternative) have been thought to converge at C3, which is cleaved to form products with multiple pro-inflammatory effects. The C5 convertase cleaves C5 to release the most potent anaphylatoxin, C5a. This induces alterations in smooth muscle and vascular tone, as well as vascular permeability and is also a powerful chemotaxin and activator of both neutrophils and monocytes. Inflammatory responses can be substantially amplified by C5a-mediated cellular activation through the induction of the release of multiple additional inflammatory mediators, including cytokines, hydrolytic enzymes, arachidonic acid metabolites and reactive oxygen species. C5 cleavage also generates C5b initiating the formation of C5b-9 known as the membrane attack complex (MAC). In addition to its role as a lytic pore-forming complex, there is strong evidence that the depositing of sublytic MAC may play an important role in inflammation.

Based upon the available clinical and research data, it appears that in most acute and chronic settings, production of C3a and C5a complement activation is mediated by the activation of the complement pathways. Because in clinical settings, both C3a and C5a have been independently shown to be involved, developing suitable methods of inhibition for all pathways would be highly desirable. Both anaphylatoxins C3a and C5a are known to activate leukocytes and platelets. A frequent indicator of cellular activation is the cellular expression of CD11b on leukocytes, and CD62P on platelets. The release of several inflammatory molecules is triggered by the platelet-leukocyte binding mediated by these activation markers. One result of such conjugate formation is the removal of platelets from the circulation, a phenomenon that can contribute to the development of thrombocytopenia.

SUMMARY OF THE INVENTION

The present invention relates to a method of inhibiting C3b dependent complement activation by limiting C3 cleavage, as well as limiting binding of C3b to factor B and C3b to properdin. C3 dependent complement activation can be inhibited by a C3 inhibitor molecule. A C3 inhibitor molecule can comprise a whole or fragmented anti-C3 antibody. The fragmented anti-C3 antibody can be $F_{ab}$, $F_{(ab)2}$, $F_v$, or single chain $F_v$. The anti-C3 antibody may be monoclonal, polyclonal, chimeric, or de-immunized and have the ability to bind C3 and its fragments. The present invention discloses the use of anti C3/C3b antibodies for the treatment of several disease conditions that involve problematic complement system activation.

One aspect of the present invention relates to a method of inhibiting the adverse effects of C3b-dependent complement activation in a subject. The method includes administering to the subject an amount of a C3b inhibitory agent effective to inhibit C3b-dependent complement activation. In this context, the phrase "C3b-dependent complement activation" refers to activation of all three complement pathways. In some aspects of the invention, the C3b inhibitory agent is an anti-C3b antibody or fragment thereof and, in other aspects, the anti-C3b antibody has reduced effector function. In still other aspects, the C3b inhibitory agent is a C3b inhibitory peptide.

The methods, compositions, and medicaments of the invention are useful for inhibiting the adverse effects of C3b-dependent complement activation in vivo in mammalian subjects, including humans suffering from an acute or chronic pathological condition or injury as further described herein. Such conditions and injuries comprise without limitation C3b mediated complement activation in associated autoimmune disorders and/or inflammatory conditions.

In one aspect of the invention, methods are provided for the treatment of ischemia reperfusion injuries of a subject experiencing ischemic reperfusion. This includes without limitation, cardiopulmonary bypass, after aortic aneurysm repair, vascular reanastomosis in connection with, for example, organ transplants such as heart, lung, liver, or kidney, extremity/digit replantation, myocardial infarction, stroke, hemodynamic resuscitation following shock and/or surgical procedures, with a therapeutically effective amount of a C3b inhibitory agent in a pharmaceutical carrier.

By treating a subject suffering from or prone to atherosclerosis with a therapeutically effective amount of a C3b inhibitory agent in a pharmaceutical carrier, the invention could provide effective inhibition of atherosclerosis. In addition, methods are provided for inhibiting C3b-dependent complement activation in a subject experiencing a vascular condition. These conditions could include without limitation, cerebrovascular conditions, cardiovascular conditions, peripheral (e.g., musculoskeletal) vascular conditions, mesenteric/enteric vascular, renovascular conditions, and revascularization to transplants and/or replants. These types of patients could be treated with a therapeutically effective amount of a C3B inhibitory agent. Such conditions include without limitation, the treatment of: vasculitis, including Henoch-Schönlein purpura nephritis, systemic lupus erythematosus-associated vasculitis, Kawasaki's disease (arteritis); dilated cardiomyopathy; vasculitis associated with rheumatoid arthritis (also called malignant rheumatoid arthritis), immune complex vasculitis, and Takayasu's disease; venous gas embolus (VGE); diabetic angiopathy; and/or restenosis following stent placement, rotational atherectomy and/or percutaneous transluminal coronary angioplasty (PTCA).

In another aspect of the invention, methods are provided for inhibiting C3b-dependent complement activation in a subject suffering from inflammatory gastrointestinal disorders, including but not limited to pancreatitis, ulcerative colitis, diverticulitis and bowel disorders including Crohn's disease, and irritable bowel syndrome. Another method that is provided by inhibiting C3b-dependent complement activation is in a subject suffering from a pulmonary condition. This includes but is not limited to acute respiratory distress syndrome, asthma, transfusion-related respiratory depression, transfusion-related acute lung injury, ischemia/reperfusion acute lung injury, meconium aspiration syndrome, bronchiolitis obliterans syndrome chronic obstructive pulmonary disease, antiglomerular basement membrane disease (Goodpasture's disease), Wegener's granulomatosis, idiopathic pulmonary fibrosis, acute lung injury secondary to burn, non-cardiogenic pulmonary edema, and emphysema.

The invention could also be applied to inhibiting C3B-dependent complement activation in a subject suffering from a musculoskeletal condition, including but not limited to osteoarthritis, rheumatoid arthritis, gout, juvenile rheumatoid arthritis, neuropathic arthropathy, psoriatic arthritis, ankylosing spondylitis or other spondyloarthropathies, and crystalline arthropathies, or systemic lupus erythematosus (SLE).

In another aspect of the invention, methods are provided for inhibiting C3b-dependent complement activation in a subject that has undergone, is undergoing or will undergo an extracorporeal reperfusion procedure, including but not limited to hemodialysis, extracorporeal membrane oxygenation (ECMO), plasmapheresis, leukopheresis, heparin-induced extracorporeal membrane oxygenation LDL precipitation (HELP) and cardiopulmonary bypass (CPB). Methods are also provided for inhibiting C3b-dependent complement activation in a subject that has received an organ or other tissue transplant, including but not limited to allotransplantation or xenotransplantation of whole organs (e.g., kidney, heart, liver, pancreas, lung, cornea, etc.) or grafts (e.g., valves, tendons, bone marrow, etc.).

In still another aspect of the invention, methods are provided for inhibiting C3b-dependent complement activation in a subject suffering from renal conditions including but not limited to membranous glomerulonephritis, mesangioproliferative glomerulonephritis, acute postinfectious glomerulonephritis (poststreptococcal glomerulonephritis), cryoglobulinemic glomerulonephritis, lupus nephritis, membranoproliferative glomerulonephritis (mesangiocapillary glomerulonephritis), Henoch-Schonlein purpura nephritis or IgA nephropathy. Also included is a subject suffering from a skin condition including but not limited to psoriasis, eosinophilic spongiosis, autoimmune bullous dermatoses, epidermolysis bullosa acquisita, bullous pemphigoid, and herpes gestationis and other skin disorders, or from a thermal or chemical burn injury involving capillary leakage.

In another aspect of the invention, methods are provided for inhibiting C3b-dependent complement activation in a subject suffering from a urogenital condition including but not limited to painful bladder disease, sensory bladder disease, chronic abacterial cystitis and interstitial cystitis, male and female infertility, placental dysfunction and miscarriage and pre-eclampsia. Another aspect of the invention, includes methods of providing inhibition of C3b-dependent complement activation in a subject suffering from nonobese diabetes (Type-1 diabetes or Insulin dependent diabetes mellitus) or from angiopathy, neuropathy or retinopathy complications of Type-1 or Type-2 (adult onset) diabetes.

In another aspect of the invention, provided are methods for inhibiting C3b-dependent complement activation in a subject suffering from a central nervous system disorder, injury, or a peripheral nervous system disorder or injury. Including but not limited to multiple sclerosis (MS), cerebral trauma, Huntington's disease (HD), myasthenia gravis (MG), Guillain Barre syndrome, amyotrophic lateral sclerosis (ALS), reperfusion following stroke, degenerative discs, cerebral trauma and/or hemorrhage, Parkinson's disease (PD), Alzheimer's disease (AD), Miller-Fisher syndrome, demyelination and meningitis. Inhibition of C3b-dependent complement activation is also applicable in a subject suffering from a blood disorder including but not limited to sepsis or a condition resulting from sepsis including without limitation severe sepsis, septic shock, acute respiratory distress syndrome resulting from sepsis, and systemic inflammatory response syndrome. Methods are also provided for the treatment of other blood disorders, including hemorrhagic shock, hemolytic anemia, autoimmune thrombotic thrombocytopenic purpura (TTP), hemolytic uremic syndrome (HUS) or other marrow/blood destructive conditions.

In another aspect of the invention, methods are provided for inhibiting C3-dependent complement activation in a subject suffering from an endocrine disorder, by administering a therapeutically effective amount of a C3b inhibitory agent in a pharmaceutical carrier to such a subject. Conditions subject to treatment in accordance with the present invention include, by way of non-limiting example, Hashimoto's thyroiditis, stress, anxiety, and other potential hormonal disorders involving regulated release of prolactin, growth or insulin-like growth factor, and adrenocorticotropin from the pituitary.

Provided, in another aspect of the invention, are methods for inhibiting C3b-dependent complement activation in a subject being treated with chemotherapeutics and/or radiation therapy. Including without limitation for the treatment of cancerous conditions. By administering a C3b inhibitor to such a patient peri chemotherapeutically or peri radiation therapy, i.e., before and/or during and/or after the administration of chemotherapeutic(s) and/or radiation therapy may be useful for reducing the side effects of chemotherapeutic or radiation therapy. In a still further aspect of the invention, methods are provided for the treatment of malignancies by administering a C3b inhibitory agent in a pharmaceutically acceptable carrier.

In another aspect of the invention methods are provided for inhibiting C3b-dependent complement activation in a subject suffering from age-related macular degeneration, thought to be the leading cause of blindness, or other complement mediated ophthalmologic condition by administering a therapeutically effective amount of a C3b inhibitory agent in a pharmaceutical carrier to a subject suffering from such a condition.

DETAILED DESCRIPTION

Figure 1:
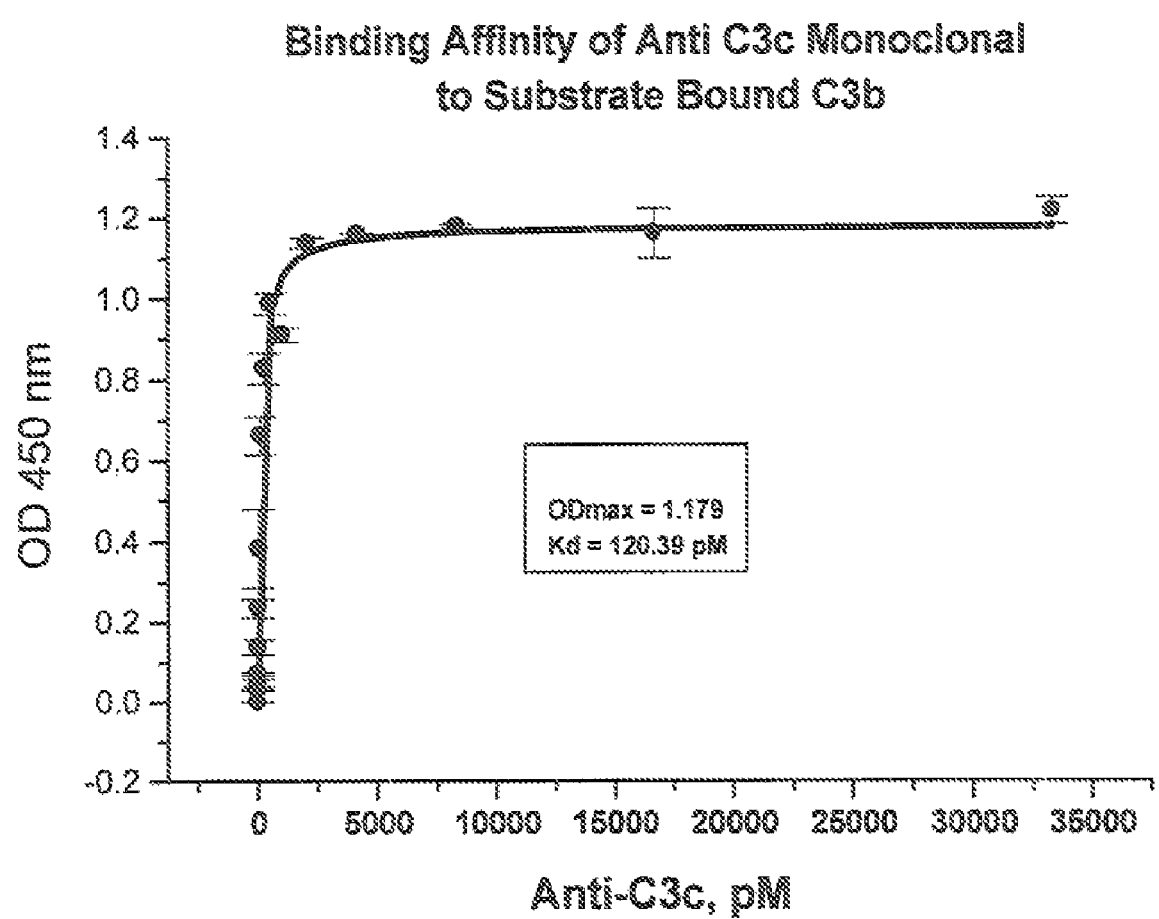
FIG. 1 illustrates a plot of a binding assay demonstrating the binding of anti-C3e antibody to C3b. The vertical (Y) axis represents the reactivity of the anti-C3c antibody to C3b
Figure 2:
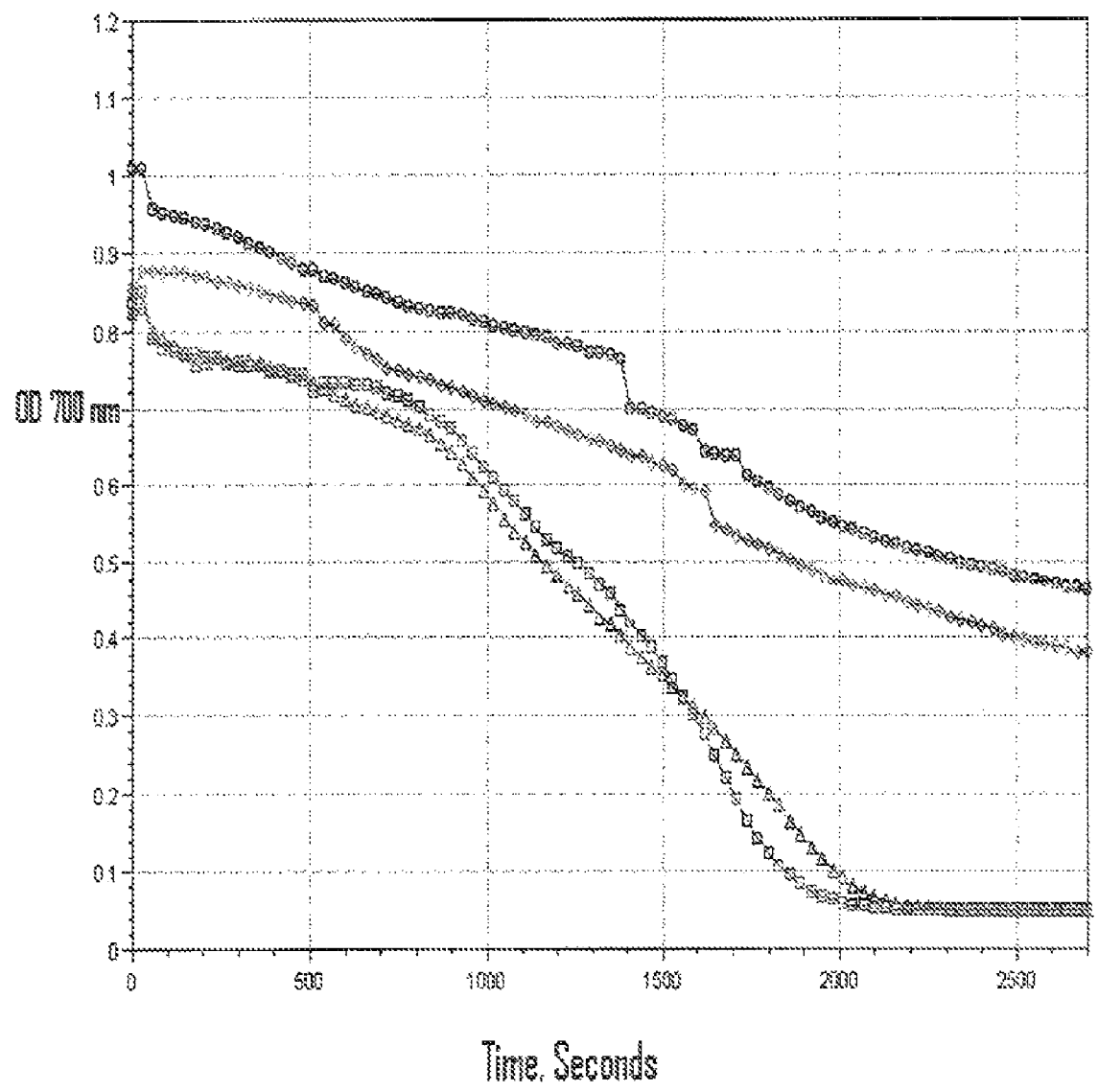
FIG. 2 illustrates a plot of the alternative pathway dependent rabbit erythrocyte hemolytic assay demonstrating anti-C3c monoclonal antibody inhibition of complement activity associated with human serum. The blocking antibody in 10% normal human serum was incubated with rabbit erythrocytes. Because of complement activation, erythrocytes lyse and cause a decrease in the light scattering. As shown in the figure, the Y-axis represents light scattering at 700 nm and the x-axis represents the incubation time at 37° C. Anti-C3c antibody inhibits rRBC hemolysis in a progressive manner.
Figure 3:
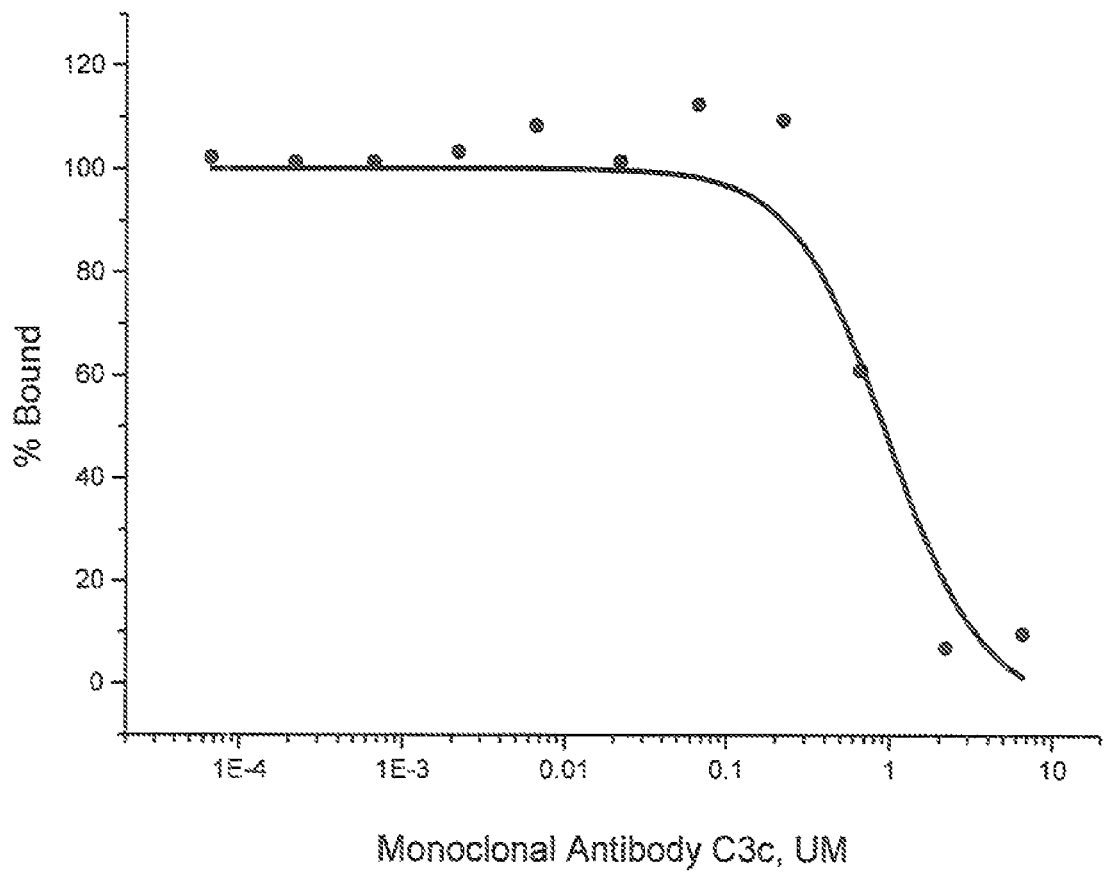
FIG. 3 illustrates a plot of the alternative pathway dependent formation of C5b-9 complex formation demonstrating anti-C3c monoclonal antibody inhibition of complement activity associated with human serum. The anti C3c antibody in 10% normal human serum was incubated with lipopolysaccharide-coated plates. Because of complement activation by LPS, C5b-9 is formed. The neoantigen on C5b-9 is detected with anti-C5b-9 antibody. As shown in the figure, the Y-axis represents the C5b-9 formation and the x-axis represents the concentration of anti-C3c antibody. As shown, anti-C3c inhibits C5b-9 formation in normal human serum.

The present invention proposes the new use of anti-C3b antibodies for the inhibition the complement biochemical cascade. The present invention describes the use of C3b as a therapeutic target for inhibiting cellular injury associated with all complement pathways. The following definitions are provided in order to provide clarity with respect to the terms as they are used in the specification and claims, in order to describe the present invention.

As used herein, the term "C3b-dependent complement activation" refers to complement activation that occurs via all possible pathways. As used herein, the term "alternative pathway" refers to complement activation, which has traditionally been thought to arise from spontaneous proteolytic generation of C3b from complement factor C3 triggered, for example, by zymosan from fungal and yeast cell walls, lipopolysaccharide (LPS) from Gram-negative outer membranes, and rabbit erythrocytes, as well as from many pure polysaccharides, rabbit erythrocytes, viruses, bacteria, animal tumor cells, parasites and damaged cells. As used herein, the term "classical pathway" refers to complement activation of the C1-complex triggered by an antibody bound to a foreign particle and requires binding of the recognition molecule C1q. As used herein, the term "classical pathway" refers to complement activation that occurs via antigen-antibody complex formation, and the term lectin pathway refers to complement activation that occurs via the specific binding of serum and non-serum carbohydrate-binding proteins including mannan-binding lectin (MBL) and the ficolins.

As used herein, the term "C3b inhibitory agent" refers to any agent that binds to or interacts with C3b and effectively inhibits C3b-dependent complement activation, including anti-C3b antibodies and C3b binding fragments thereof, natural and synthetic peptides. C3b inhibitory agents useful in the method of the invention may reduce C3b-dependent complement activation, therefore all activation, by greater than 20%. In one embodiment, the C3b inhibitory agent reduces complement activation by greater than 90%.

As used herein, the term "antibody" encompasses antibodies and antibody fragments, that specifically bind to C3b or its polypeptides or portions, in which the antibody is derived from any antibody-producing mammal (e.g., mouse, rat, rabbit and primate including human). Exemplary antibodies include polyclonal, monoclonal and recombinant antibodies; multispecific antibodies (e.g., bispecific antibodies), humanized antibodies; murine antibodies, chimeric (i.e. mouse-human, mouse-primate, primate-human), monoclonal antibodies, and anti-idiotype antibodies, as well as de-immunized antibodies, and may be any intact molecule or fragment thereof.

As used herein, the term "antibody fragment" refers to a portion derived from or related to a full-length anti-C3b antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "humanized antibody" is a chimeric antibody that comprises a minimal sequence conforming to specific complementarity-determining regions derived from non-human immunoglobulin that is transplanted into a human antibody framework. Humanized antibodies are typically recombinant proteins in which only the antibody complementarity-determining regions are of non-human origin. As used herein, a "chimeric antibody" is a recombinant protein that contains the variable domains and complementarity-determining regions derived from a non-human species (e.g., rodent) antibody, while the remainder of the antibody molecule is derived from a human antibody. As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, the "membrane attack complex" ("MAC") refers to a complex of the five terminal complement components ($C_5$-$C_9$) that inserts into and disrupts membranes also referred to as C5b-9. As used herein, "a subject" includes all mammals, including without limitation dogs, cats, horses, sheep, goats, cows, rabbits, pigs, humans, non-human primates, and rodents. The alternative pathway can also provide an amplification loop for complement activation initially triggered via the classical and lectin pathways, in addition to its widely accepted role as an independent pathway for complement activation. In this alternative pathway-mediated amplification mechanism, the activation generated C3 convertase (C4b2b) from either the classical or the lectin complement cascades cleaves C3 into C3a and C3b, and thereby provides C3b that can participate in forming C3bBb, the alternative pathway C3 convertase.

In addition to its essential role in immune defense, the complement system contributes to tissue damage in many clinical conditions. The activities included in the complement biochemical cascade present a potential threat to host tissue. An example includes the indiscriminate release of destructive enzymes possibly causing host cell lysis. Thus, there is a pressing need to develop therapeutically effective complement inhibitors to prevent these adverse effects.

Ischemia reperfusion injury (I/R) is tissue damage that occurs when blood supply returns to the tissue after an extended period of ischemia and is a common source of morbidity and mortality in a wide spectrum of diseases. Patients are vulnerable to I/R after surgery such as cardiopulmonary bypass, aortic aneurysm repair, vascular reanastomosis in connection with, for example, organ transplants (e.g., heart, lung, liver, and kidney) and digit/extremity replantation, stroke, myocardial infarction and hemodynamic resuscitation following shock and/or surgical procedures. Patients with atherosclerotic diseases are prone to strokes, myocardial infarctions, and emboli-induced intestinal and lower-extremity ischemia and those who experience trauma, frequently suffer from temporary ischemia of the limbs. Additionally any case of large amounts of blood loss can lead to a severe whole-body I/R reaction. The pathophysiology of I/R injury is complex, with at least two major factors contributing to the process: complement activation and neutrophil stimulation with accompanying oxygen radical-mediated injury.

In I/R injury, complement activation was first described during myocardial infarction over 30 years ago, and has led to numerous investigations on the contribution of the complement system to I/R tissue injury. Through investigation, growing evidence identifies complement as a pivotal mediator in I/R injury as inhibition of complement activation has been successful in limiting tissue damage and injury in numerous I/R animal models. In early studies, C3 depletion was obtained following infusion of cobra venom factor, reported to be beneficial during I/R in kidney and heart. However, the soluble form of complement receptor 1 (sCR1) was the first complement-specific inhibitor utilized for the prevention of myocardial I/R injury decreased deposition of C5b-9 complexes along the coronary endothelium and decreased leukocyte infiltration after reperfusion was associated with sCR1 treatment during myocardial I/R attenuates infarction. Animals genetically deficient in C3 have less local tissue necrosis after skeletal muscle or intestinal ischemia.

The membrane attack complex is the most significant vehicle of complement-directed injury and studies in animals with a C5-deficiency have shown decreased local and remote injury in models of I/R injury. An inhibitor of complement activation, soluble Crry (complement receptor-related gene Y), has shown effectiveness against injury when given both before and after the onset of murine intestinal reperfusion. In a model of skeletal muscle ischemia, the use of soluble complement receptor 1 (sCR1) also reduced muscle injury when given after the start of reperfusion. In a porcine model of myocardial I/R, animals treated with monoclonal antibody ("MoAb") to the anaphylatoxin C5a prior to reperfusion showed attenuated infarction. Rats treated with C5 MoAb demonstrated attenuated infarct size, neutrophil infiltration, and apoptosis in the myocardium.

The results of these experiments illustrate the importance of complement activation in the development of I/R injury. However, it is not specifically clear which complement pathway (classical, lectin or alternative) is predominantly involved in complement activation during cases of I/R injury.

In order to prevent the possible problems resulting from myocardial I/R complications, several inhibitors of complement activation have been developed as potential therapeutic agents. Two of these inhibitors, sCR1 (TP10) and humanized anti-C5 scFv (Pexelizumab), have completed Phase II clinical trials and pexelizumab has completed a Phase III clinical trial. Results from a Phase II trial of TP 10 ending in February 2002 failed to meet its primary endpoint even though it was well tolerated and beneficial to patients in early Phase I/II trials. However, sub-group analysis of the data from male patients in a high-risk population undergoing open-heart procedures showed significant reductions in mortality and infarct size. Administration of a humanized anti-C5 scFv decreased overall patient mortality associated with acute myocardial infarction in the COMA and COMPLY Phase II trials, but failed to meet the primary endpoint. Results from a recent Phase III anti-C5 scFv clinical trial (PRIMO-CABG) for improving surgically induced outcomes following coronary artery bypass were recently released. The study showed significant improvement in areas of reducing postoperative patient morbidity and mortality even though the primary endpoint for this study was not reached.

One aspect of the invention is thus directed to the treatment of ischemia reperfusion injuries by treating a subject experiencing ischemic reperfusion with a therapeutically effective amount of a C3b inhibitory agent commencing immediately after or as soon as possible after an ischemia reperfusion event. In instances where reperfusion occurs in a controlled environment (e.g., following an aortic aneurism repair, organ transplant or reattachment of severed or traumatized limbs or digits), the C3b inhibitory agent may be administered prior to and/or during and/or after reperfusion. The C3b inhibitory agent can be administered in various ways by intra-arterial, intracranial, intravenous, subcutaneous, intramuscular, or other parenteral administration. Potentially orally for non-peptidergic inhibitors, and most suitably by intra-arterial or intravenous administration. Administration may be repeated periodically as determined by a physician for optimal therapeutic effect.

Disease Conditions

Atherosclerosis

There is considerable evidence that complement activation is involved in atherogenesis in humans. Components of the terminal complement pathway are frequently found in human atheromas, C3 and C4 deposition in arterial lesions has also been demonstrated. The extent of C5b-9 deposition was found to correlate with the severity of the lesion. In ruptured and vulnerable plaques, deposition of complement iC3b, but not C5b-9, was especially strong, suggesting that complement activation may be a factor in acute coronary syndromes. In experimental atheroma in rabbits, complement activation was found to precede the development of lesions.

Other Vascular Diseases and Conditions

Complement-mediated vascular injury has been shown to contribute to the pathophysiology of several diseases of the cardiovascular system, including atherosclerosis, ischemia-reperfusion injury, and myocardial infarction. Evidence suggests that complement activation may extend to other vascular conditions, for example, pathogenesis of many forms of vasculitis, including: Henoch-Schönlein purpura nephritis, immune complex vasculitis, vasculitis associated with rheumatoid arthritis (also called malignant rheumatoid arthritis), systemic lupus erythematosus-associated vasculitis, and Takayasu's disease.

Frequently associated with severe vasculitis, systemic lupus erythematosus (SLE) is an example of systemic autoimmune diseases that affects multiple organs including skin, kidneys, joints, serosal surfaces, and central nervous system. IgG anti-endothelial antibodies and IgG complexes capable of binding to endothelial cells are present in the sera of patients with active SLE, and deposits of IgG immune complexes and complement are found in blood vessel walls of patients with SLE vasculitis. Another pleomorphic group of human diseases in which complement-dependent cytotoxicity against endothelial and other cell types plays a documented role includes such diseases as rheumatoid arthritis associated with vasculitis, also called malignant rheumatoid arthritis, immune-complex vasculitis, leukocytoclastic vasculitis, vasculitis associated with hepatitis A, and the arteritis known as Takayasu's disease.

Other evidence has suggested that complement activation plays a role in dilated cardiomyopathy, characterized by impaired systolic function of the heart and cardiac enlargement. Recent data suggests that ongoing inflammation in the myocardium may contribute to the development of disease. Strong correlation has been identified between C5b-9, the terminal membrane attack complex of complement activation, and immunoglobulin deposition and myocardial expression of TNF-alpha. Suggesting that chronic immunoglobulin-mediated complement activation in the myocardium may contribute in part to the progression of dilated cardiomyopathy, myocardial accumulation of C5b-9 was demonstrated in myocardial biopsies from 28 patients with dilated cardiomyopathy.

One aspect of the invention is thus directed to the treatment of a vascular condition, including peripheral vascular conditions, renovascular conditions, cardiovascular conditions, cerebrovascular conditions, and mesenteric/enteric vascular conditions, by administration of a composition comprising a therapeutically effective amount of a C3b inhibitory agent in a pharmaceutical carrier. Examples of conditions for the current invention include, without limitation: vasculitis, including Henoch-Schonlein purpura nephritis, vasculitis associated with rheumatoid arthritis (also called malignant rheumatoid arthritis), immune complex vasculitis, systemic lupus erythematosus-associated vasculitis, and Takayasu's disease, dilated cardiomyopathy; diabetic angiopathy; Kawasaki's disease (arteritis); and venous gas embolus (VGE).

Gastrointestinal Disorders

Inflammatory bowel disease (IBD) includes chronic inflammatory disorders of the bowel that include ulcerative colitis and Crohn's disease, often characterized by spontaneously occurring, chronic, relapsing inflammation of unknown origin. The activation of the complement system in patients with IBD is thought to play a role in disease pathogenesis. It has been shown that C3b and other activated complement products are found at the luminal face of surface epithelial cells, in the muscularis mucosa as well as the sub mucosal blood vessels in IBD patients.

Pulmonary Conditions

Complement activation has been implicated in the pathogenesis of many lung inflammatory disorders including:

asthma; Wegener's granulomatosis; chronic obstructive pulmonary disease (COPD); acute respiratory distress syndrome (ARDS); transfusion-related acute lung injury (TRALI); ischemia/reperfusion acute lung injury; and antiglomerular basement membrane disease (Goodpasture's disease). It is now well accepted that much of the pathophysiology of ARDS involves a dysregulated inflammatory cascade that begins as a normal response to an infection or other inciting event, but ultimately causes significant auto injury to the host. Patients with ARDS almost universally show evidence of extensive complement activation such as increased plasma levels of complement components C3a and C5a. The degree of complement activation has been correlated with the development and outcome of ARDS. Asthma is essentially an inflammatory disease and evidence that the complement system is highly active in the human asthmatic lung is well documented. Recent data from animal models and humans provide evidence that complement activation is a significant mechanism contributing to disease pathogenesis.

Experimental and clinical data suggests a role for complement activation in the pathophysiology of ARDS. Various animal models have illustrated that systemic activation of complement leads to acute lung injury with histopathology similar to that seen in human ARDS. Inhibiting the complement biochemical cascade by general complement depletion or by specific inhibition of C5a provides protection in animal models of acute lung injury.

Extracorporeal Circulation

Various medical procedures divert blood from a patient's circulatory system known as extracorporeal circulation systems (ECC). Some of these procedures include hemodialysis, leukopheresis, plasmapheresis, heparin-induced extracorporeal membrane oxygenation LDL precipitation (HELP), extracorporeal membrane oxygenator (ECMO), and cardiopulmonary bypass (CPB). These procedures involve the exposure of blood products or blood itself to foreign surfaces that have the capacity to alter normal cellular function and hemostasis. Studies have identified complement activation as the probable cause of granulocytopenia during hemodialysis. Indications that activation of the complement system caused many of the adverse events experienced by patients undergoing hemodialysis or CPB have been identified in recent studies. For example, the potential of complement system activation has been shown to be an important criterion in determination of the biocompatibility of hemodialyzers with respect to recovery of renal function, susceptibility to infection, pulmonary dysfunction, morbidity, and survival rate of patients with renal failure.

Partly caused by exposure of blood to artificial surfaces as well as surface-independent factors like surgical trauma and ischemia-reperfusion injury, patients undergoing ECC during CPB suffer a systemic inflammatory reaction. The CPB-triggered inflammatory reaction can result in post surgical complications, generally termed "postperfusion syndrome". Included in postoperative events are cognitive deficits, bleeding disorders, respiratory failure, renal dysfunction and, in the most severe cases, multiple organ failure. Coronary bypass surgery with CPB leads to profound activation of the complement system, in contrast to surgery with a comparable degree of surgical trauma but without CPB. Therefore, the primary suspected cause of these CPB-related problems is inappropriate activation of complement during the bypass procedure. In CPB circuits, the alternative complement pathway plays a predominant role in complement activation because of the exposure of blood with artificial surfaces within the CPB circuits. However, there is also evidence that the classical complement pathway is activated during CPB.

Following activation of the complement system, primary inflammatory substances are generated including anaphylatoxins C3a and C5a, the opsonin C3b, as well as the membrane attack complex C5b-9. C3a and C5a are potent stimulators of neutrophils, monocytes, and platelets release of pro-inflammatory cytokines (IL-1, IL-6, IL-8, TNF alpha), oxidative free radicals and proteases results from the activation of the inflammatory substances. C5a has been shown to upregulate adhesion molecules CD11b and CD18 of Mac-1 in polymorphonuclear cells (PMNs), as well as induce degradation of PMNs releasing pro-inflammatory enzymes. C5b-9 induces the expression of adhesion molecule P-selectin (CD62P) on platelets, whereas both C5a and C5b-9 induce surface expression of P-selectin on endothelial cells. These adhesion molecules are involved in the interaction among leukocytes, platelets, and endothelial cells, while their expression is responsible for sequestration of activated leukocytes mediating tissue inflammation and injury. It is the actions of these complement activation products on neutrophils, monocytes, platelets and other circulatory cells that likely lead to the various problems that arise after CPB.

Inflammatory and Non-Inflammatory Arthritides and Other Musculoskeletal Diseases Activation of the complement system has been implicated in the pathogenesis of a wide variety of rheumatological diseases; including rheumatoid arthritis, juvenile rheumatoid arthritis, osteoarthritis, systemic lupus erythematosis (SLE), Behcet's syndrome and Sjogren's syndrome. There is compelling evidence that immune-complex-triggered complement activation is a major pathological mechanism that contributes to tissue damage in rheumatoid arthritis (RA). Documentation from numerous publications shows that complement activation products are elevated in the plasma of rheumatoid arthritis patients. Complement activation products such as C3a, C5a, and sC5b-9 have also been found within inflamed rheumatic joints and positive correlations have been established between the degree of complement activation and the severity of RA. Indications that complement activation is mediated predominantly by the alternative pathway include, in both adult and juvenile rheumatoid arthritis, elevated serum and synovial fluid levels of alternative pathway complement activation product Bb compared to C4d (a marker for classical pathway activation) through recruitment of inflammatory cells by the anaphylatoxins C3a and C5a or directly damage tissue (via C5b-9), complement activation products can indirectly mediate inflammation.

Systemic lupus erythematosus (SLE) is an autoimmune disease of undefined etiology that results in episodic, uncontrolled activation of the complement system, production of autoantibodies, and generation of circulating immune complexes. Although the origins of autoimmunity in SLE remain elusive, considerable information is now available implicating complement activation as an important mechanism contributing to vascular injury in this disease. Activation of both the classical and alternative pathways of complement is involved in the disease and both C4d and Bb are sensitive markers of moderate-to-severe lupus disease activity. Activation of the alternative complement pathway accompanies disease flares in systemic lupus erythematosus during pregnancy. Immune complex-mediated activation of complement through the classic pathway is believed to be one mechanism by which tissue injury occurs in SLE patients. Results from animal models of SLE support the important role of complement activation in pathogenesis of the disease. Inhibiting the activation of C5 using a blocking anti-C5 MoAb decreased proteinuria and renal disease in NZB/NZW F1 mice, a mouse model of SLE.

Renal Conditions

Activation of the complement system has been implicated in the pathogenesis of a wide variety of renal diseases; including, mesangioproliferative glomerulonephritis (IgA-nephropathy, Berger's disease), membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, and Henoch-Schonlein purpura nephritis. There continues to be a major discussion on complements exact role in the onset of renal disease despite acknowledgement of complement system involvement. Under normal conditions, the contribution of complement is beneficial to the host, but inappropriate activation and deposition may contribute to host cell and tissue damage. Substantial evidence exists that shows glomerulonephritis, inflammation of the glomeruli, is often initiated by deposition of immune complexes onto glomerular or tubular structures, triggering complement activation, inflammation, and tissue damage. Kahn and Sinniah demonstrated increased deposition of C5b-9 in tubular basement membranes in biopsies taken from patients with various forms of glomerulonephritis.

C5b-9 deposition in the tubular epithelial/basement membrane structures correlated with plasma creatinine levels in a study of patients with IgA nephrology. Another study of membranous nephropathy demonstrated a relationship between clinical outcome and urinary sC5b-9 levels. Elevated sC5b-9 levels were highly correlated with reduced prognosis. Lehto et al., measured in urine from patients with membranous glomerulonephritis, elevated levels of a complement regulatory factor that inhibits the membrane attack complex in plasma membranes (CD59), as well as C5b-9. Deposition of C3 and C9 proteins in the glomeruli was revealed after histopathological analysis of biopsy samples taken from the same patients, whereas expression of CD59 in these tissues was diminished compared to that of normal kidney tissue. Ongoing complement-mediated glomerulonephritis results in urinary excretion of complement proteins correlating with the degree of tissue damage as well as disease prognosis, as suggested by these various studies.

In addition, demonstration of the importance of complement activation in the etiology of the disease was found in inhibition of complement activation during various animal models of glomerulonephritis. In a model of membranoproliferative glomerulonephritis (MPGN), infusion of anti-Thy1 antiserum in C6-deficient rats (that cannot form C5b-9) compared to C6+normal rats, resulted in 90% less glomerular cellular proliferation, 80% reduction in platelet and macrophage infiltration, diminished collagen type IV synthesis (a marker for mesangial matrix expansion), and 50% less proteinuria. These results implicate C5b-9 as a major mediator of tissue damage by complement activation.

In another model of glomerulonephritis, infusion of graded dosages of rabbit anti-rat glomerular basement membrane produced a dose-dependent influx of polymorphonuclear leukocytes (PMN) that was attenuated by prior treatment with cobra venom factor (to consume complement). Showing diminished histopathology, decreased long-term proteinuria, and lower creatinine levels, the cobra venom factor-treated rats differed from the control rats. Demonstrating the potential therapeutic efficacy of approaches to inhibit complement by using the recombinant sCR1 protein, Couser et al., employed three models of GN in rats (anti-thymocyte serum, Con A anti-Con A, and passive Heymann nephritis). Rats treated with sCR1 resulted in a significant reduction of PMN, platelet and macrophage influx, decreased mesangiolysis, and proteinuria versus control rats. Further evidence has been provided for the importance of complement activation in glomerulonephritis by the use of an anti-C5 MoAb in the NZB/W F1 mouse model. The anti-C5 MoAb inhibits cleavage of C5, therefore blocking the production of C5a and C5b-9. Continuous therapy with anti-C5 MoAb over the period of 6 months resulted in significant amelioration of the course of glomerulonephritis. A humanized anti-C5 MoAb monoclonal antibody (5G1.1) is under development by Alexion Pharmaceuticals, Inc., New Haven, Conn., that prevents the cleavage of human complement component C5 into its pro-inflammatory components. The antibody is considered a potential treatment for glomerulonephritis Direct evidence has been found by studies of patients with genetic deficiencies in specific complement components, for a pathological role of complement in renal injury. A number of reports have documented an association of deficiencies of complement regulatory factor H with renal disease. Factor H deficiency results in low plasma levels of factor B and C3 and in consumption of C5b-9 as well as an association with atypical membranoproliferative glomerulonephritis (MPGN) and idiopathic hemolytic uremic syndrome (HUS). Confirming the importance of factor H in complement regulation, factor H deficient pigs and factor H knockout mice display MPGN-like symptoms. Deficiencies of other complement components are associated with renal disease, secondary to the development of systemic lupus erythematosus (SLE). Through mechanisms relating to defective clearance of immune complexes and apoptotic material, deficiency for C1q, C4 and C2 predispose strongly to the development of SLE. In many of these SLE patients lupus nephritis occurs, which is characterized by the deposition of immune complexes throughout the glomerulus.

One aspect of the invention is thus directed to the treatment of renal conditions. Including but not limited to mesangioproliferative glomerulonephritis, membranous glomerulonephritis, lupus nephritis, membranoproliferative glomerulonephritis (mesangiocapillary glomerulonephritis), cryoglobulinemic glomerulonephritis, acute postinfectious glomerulonephritis (poststreptococcal glomerulonephritis), Henoch-Schonlein purpura nephritis, or IgA nephropathy. By administering a composition comprising a therapeutically effective amount of a C3b inhibitory agent in a pharmaceutical carrier to a subject suffering from such a disorder. The C3b inhibitory agent may be administered to the subject systemically, such as by intramuscular, intra-arterial, intravenous, subcutaneous or other parenteral administration, or potentially by oral administration for non-peptidergic agents. The C3b inhibitory agent may be administered periodically over an extended period of time for treatment or control of a chronic condition, or may be by single or repeated administration in the period before, during, or following acute trauma or injury.

Skin Disorders

Psoriasis is a chronic, debilitating skin condition affecting millions of people and has been attributed to both genetic and environmental factors. First-line of treatment for psoriasis generally includes topical agents as well as UVB and PUVA phototherapy. However, systemic therapy can be used as a primary treatment or used to augment UVB and PUVA therapy for generalized or more extensive disease. The underlying etiology of various skins diseases such as psoriasis supports a role for immune and pro-inflammatory processes including the involvement of the complement system. Often described as an immune-mediated disorder, it is thought that abnormal activity causes inflammation and cell growth activation. Moreover, the role of the complement system has been established as an important nonspecific skin defense mechanism. Its activation leads to the generation of products that aid in the maintenance of normal host defenses as well as mediate inflammation and tissue injury. Pro-inflammatory products of complement activation include large fragments of C3 with opsonic and cell-stimulatory activities (C3b and C3bi), low molecular weight anaphylatoxins (C3a, C4a, and C5a), and membrane attack complexes. Seemingly, the most important mediator is C5a or its degradation product C5a des Arg, because it exerts a potent chemotactic effect on inflammatory cells. Intradermal administration of C5a anaphylatoxin induces skin changes rather similar to those observed in cutaneous hypersensitivity vasculitis that occurs through immune complex-mediated complement activation.

Complement activation is involved in the pathogenesis of the inflammatory changes during autoimmune bullous dermatoses. Complement activation by pemphigus antibody in the epidermis seems to be responsible for the development of characteristic inflammatory changes termed eosinophilic spongiosis. In bullous pemphigoid (BP), seemingly related to leukocytes lining the dermoepidermal junction, interaction of basement membrane zone antigen and BP antibody leads to complement activation. The resulting anaphylatoxins activate the infiltrating leukocytes, as well as induce mast cell degranulation facilitating dermoepidermal separation and eosinophil infiltration. Similarly, complement activation seems to play a more direct role in the dermoepidermal separation noted in epidermolysis bullosa acquisita and herpes gestationis. Evidence for the involvement of complement in psoriasis comes from recent experimental findings described in the literature related to the pathophysiological mechanisms for the inflammatory changes in psoriasis and related diseases. The importance of T-cell-mediated immunity in the triggering and maintaining of psoriatic lesions is gathering support and further evidence. It has been revealed that lymphokines produced by activated T-cells in psoriatic lesions have a strong influence on the proliferation of the epidermis. Characteristic neutrophil accumulation under the stratum corneum can be observed in the highly inflamed areas of psoriatic lesions. Neutrophils are chemotactically attracted and activated there by synergistic action of chemokines, IL-8 and Gro-alpha released by stimulated keratinocytes, and particularly by C5a/C5a des-arg produced via the alternative complement pathway activation.

Psoriatic scale extracts contain a unique chemotactic peptide fraction that is likely to be involved in the induction of rhythmic transepidermal leukocyte chemotaxis. Recent studies have identified the presence of two unrelated chemotactic peptides in this fraction, i.e., C5a/C5a des Arg and interleukin 8 (IL-8) and its related cytokines. Concentrations of immunoreactive C5a/C5a desArg and IL-8 in psoriatic lesional scale extracts and those from related sterile pustular dermatoses were quantified to investigate their relative contribution to the transepidermal leukocyte migration as well as their interrelationship in psoriatic lesions. It was found that the concentrations of C5a/C5a desArg and IL-8 were more significantly increased in the horny-tissue extracts from lesional skin than in those from non-inflammatory orthokeratotic skin. The increase of C5a/C5a desArg concentration was specific to the lesional scale extracts. Based on these results, it appears that C5a/C5a desArg is generated only in the inflammatory lesional skin, under specific circumstances that favor complement activation. This provides a rationale for the use of an inhibitor of complement activation to ameliorate psoriatic lesions.

While it has been shown that the classical pathway of the complement system is activated in psoriasis, there are fewer reports on the involvement of the alternative pathway in the inflammatory reactions in psoriasis. Within the conventional view of complement activation pathways, complement fragments C4d and Bb are released at the time of the classical and alternative pathway activation, respectively. The presence of the C4d or Bb fragment, therefore, denotes a complement activation that proceeds through the classical and/or alternative pathway. One study measured the levels of C4d and Bb in psoriatic scale extracts using enzyme immunoassay techniques. The scales of these dermatoses contained higher levels of C4d and Bb detectable by enzyme immunoassay than those in the stratum corneum of noninflammatory skin. These results suggest that the alternative pathway is activated in addition to the classical pathway of complement in psoriatic lesional skin. Additional evidence for the involvement of complement in psoriasis and atopic dermatitis has been obtained by measuring normal complement components and activation products in the peripheral blood of 35 patients with atopic dermatitis (AD) and 24 patients with psoriasis at a mild to intermediate stage. Levels of C3, C4 and C1 inactivator (C1 INA) were determined in serum by radial immunodiffusion, whereas C3a and C5a levels were measured by radioimmunoassay. The levels of C3, C4 and C1 INA were found to be significantly increased in both diseases in comparison to healthy non-atopic controls. In AD, there was a tendency towards increased C3a levels, whereas in psoriasis, C3a levels were significantly increased. The results indicate that, in both AD and psoriasis, the complement system participates is the inflammatory process.

By measuring levels of SC5b-9 in the plasma and horny tissues of psoriatic patients, complement activation in psoriatic lesional skin also results in the deposition of terminal complement complexes within the epidermis. The levels of SC5b-9 in psoriatic plasma have been found to be significantly higher than those of controls or those of patients with atopic dermatitis. Studies of total protein extracts from lesional skin have shown that, there were high levels of SC5b-9 in lesional horny tissues of psoriasis, despite no SC5b-9 detected in the noninflammatory horny tissues. By using a monoclonal antibody to the C5b-9 neoantigen in immunofluorescence, deposition of C5b-9 has been observed only in the stratum corneum of psoriatic skin. To summarize, psoriatic lesional skin shows complement system activation that proceeds all the way to the terminal step, leading to membrane attack complex.

New drugs that selectively target the immune system have recently become available for treating psoriasis including four biologic drugs either currently FDA approved or in Phase 3 studies. Those include alefacept (Amevive) and efalizuMoAb (Raptiva) which are T-cell modulators, etanercept (Enbrel), a soluble TNF-receptor; and inflixiMoAb (Remicade), an anti-TNF monoclonal antibody. Raptiva is an immune response modifier, wherein the targeted mechanism of action is a blockade of the interaction between LFA-1 on lymphocytes and ICAM-1 on antigen-presenting cells and on vascular endothelial cells. Binding of CD11a by Raptiva results in saturation of available CD11a binding sites on lymphocytes, as well as down-modulation of cell surface CD11a expression on lymphocytes. This causes inhibition of T-cell activation, cell trafficking to the dermis and epidermis and T-cell reactivation. Therefore, various instances scientific evidence indicates inflammatory disease states of the skin involves complement activation leading to recent pharmaceutical approaches that target the immune system or specific inflammatory processes. None, however, have identified C3b as a targeted approach. Based on the inventors' understanding of the role of C3b in complement activation, the inventors identify C3b as an effective target for the treatment of psoriasis and other skin disorders.

One aspect of the invention is thus directed to the treatment of psoriasis, autoimmune bullous dermatoses, eosinophilic spongiosis, bullous pemphigoid, epidermolysis bullosa acquisita, atopic dermatitis, herpes gestationis and other skin disorders. As well as for the treatment of thermal and chemical burns including capillary leakage caused thereby, by administering a composition comprising a therapeutically effective amount of a C3b inhibitory agent in a pharmaceutical carrier to a subject suffering from such a skin disorder. The C3b inhibitory agent may be administered to the subject topically, by application of a spray, lotion, gel, paste, salve or irrigation solution containing the C3B inhibitory agent, or systemically such as by intra-arterial, intravenous, intramuscular, subcutaneous or other parenteral administration, or potentially by oral administration for non-peptidergic inhibitors. Treatment may involve a single administration or if necessary repeated applications or dosing for an acute condition or by periodic applications or dosing for control of a chronic condition.

Transplantation

Inflammatory reaction after solid organ transplantation is due to significant contribution by the activation of the complement system. In allotransplantation, activation of the complement system may be caused by ischemia/reperfusion and possibly, antibodies directed against the graft. In xenotransplantation from nonprimates to primates, the major activators for the complement system are already existing antibodies. Studies in animal models have shown that the use of complement inhibitors may significantly prolong graft survival, thus, establishing the role of the complement system in organ injury after organ transplantation. Therefore, the inventors believe by utilizing C3b directed complement inhibitors damage prevention is possible in situation of grafts after allo- or xenotransplantation.

Innate immune mechanisms, particularly complement, play a greater role in inflammatory and immune responses against the graft than has been previously recognized. It appears that alternative complement pathway activation mediates renal ischemia/reperfusion injury, and in this setting proximal tubular cells may be both the source and the site of attack of complement components. Locally produced complement in the kidney also plays a role in the development of both cellular and antibody-mediated immune responses against the graft. C4d is the degradation product of the activated complement factor C4, a component of the classical and lectin-dependent pathways. The association between C4d and morphological signs of acute cellular rejection is statistically significant. C4d staining has emerged as a useful marker of humoral rejection both in the acute and in the chronic setting and led to renewed interest in the significance of anti-donor antibody formation. C4d is found in 24-43% of Type I episodes, in 45% of type II rejection and 50% of type III rejection. A number of therapies are in development that inhibit complement or reduce local synthesis as a means to achieve an improved clinical outcome following transplantation.

Complement plays a critical role in xenograft rejection, making effective complement inhibitors great targets as potential therapeutic agents. In pig-to-primate organ transplantation, hyperacute rejection (HAR) results from complement activation and antibody deposition. Multiple strategies and targets have been tested to prevent hyperacute xenograft rejection in the pig-to-primate combination. These approaches have been accomplished by removal of natural antibodies, complement depletion with cobra venom factor, or prevention of C3 activation with the soluble complement inhibitor sCR1. In addition, complement activation blocker-2 (CAB-2), a recombinant soluble chimeric protein derived from human decay accelerating factor (DAF) and membrane cofactor protein, inhibits C3 and C5 convertases of both classical and alternative pathways. A pig heart perfused ex vivo with human blood shows reduced complement-mediated tissue injury due to CAB-2. A study of the efficacy of CAB-2 including the transplantation of a pig heart into rhesus monkeys showed that graft survival was markedly prolonged in monkeys that received CAB-2 compared to those receiving no immunosuppression. CAB-2 markedly inhibited complement activation, as shown by a strong reduction in generation of C3a and SC5b-9. At graft rejection, tissue deposition of iC3b, C4 and C9 was similar or slightly reduced from controls, and deposition of IgG, IgM, C1q and fibrin did not change. Thus, this approach for complement inhibition abrogated hyperacute rejection of pig hearts transplanted into rhesus monkeys. These studies demonstrate the beneficial effects of complement inhibition on survival and the inventors believe that C3b inhibition may also be useful in xenotransplantation.

The availability of specific inhibitors of complement may provide the opportunity for an improved clinical outcome following organ transplantation. Inhibitors that act by a mechanism that blocks complement attack may be particularly useful, because they hold the promise of increased efficacy and avoidance of systemic complement depletion in an already immuno-compromised recipient.

Another approach has focused on determining if anti-complement 5 (C5) monoclonal antibodies could prevent hyperacute rejection (HAR) in a rat-to-presensitized mouse heart transplantation model. Also to determine if these MoAb, combined with cyclosporine and cyclophosphamide, could achieve long-term graft survival. Results found that anti-C5 MoAb prevents HAR, leading the inventors to believe that other targets in the complement cascade, such as C3b, may also be valuable for preventing HAR and acute vascular rejection in future clinical cases of xenotransplantation.

While the pivotal role of complement activation in hyperacute rejection seen in xenografts is well established, a more subtle role in allogeneic transplantation is beginning to be identified. A link between complement and the acquired immune response has long been known, with the finding that complement-depleted animals mounted subnormal antibody responses following antigenic stimulation. Impressive increases in effectiveness from opsonization of antigen with the complement split product C3d, has been shown on antigen presentation to B cells, and has been known to act via engagement of complement receptor type 2 on certain B cells. Extension of this work to the transplantation setting in a skin graft model in mice has illustrated effectiveness, where C3- and C4-deficient mice had a marked defect in allo-antibody production, due to failure of class switching to high-affinity IgG. The importance of these mechanisms in renal transplantation is increased due to the significance of anti-donor antibodies and humoral rejection.

Demonstration of upregulation of C3 synthesis by proximal tubular cells during allograft rejection following renal transplantation has already been identified in previous work. The role of locally synthesized complement has been examined in a mouse renal transplantation model. Grafts from C3-negative donors transplanted into C3-sufficient recipients showed significant improvements in survival duration (>100 days) as compared with the control grafts from C3-positive donors, which were rejected within 14 days. Furthermore, the anti-donor T-cell proliferative response in recipients of C3-negative grafts was markedly reduced as compared with that of controls, indicating an effect of locally synthesized C3 on T-cell priming.

In the setting of renal transplantation, tubular cells that produce complement also demonstrate complement deposition on their cell surface. These observations suggest the possibility that exposure of donor antigen to T-cells first occurs in the graft and that locally synthesized complement enhances antigen presentation, either by opsonization of donor antigen or by providing additional signals to both antigen-presenting cells and T-cells.

Tissue or solid organ transplantation mediated inflammatory reaction is also prevented. By administering a composition comprising a therapeutically effective amount of a C3b inhibitory agent in a pharmaceutical carrier to the transplant recipient, including subjects that have received allotransplantation or xenotransplantation of whole organs (e.g., kidney, heart, liver, pancreas, lung, cornea, etc.) or grafts (e.g., valves, tendons, bone marrow, etc.). Administration may occur during the acute period following transplantation or as long-term post transplantation therapy. The C3b inhibitory agent may be administered to the subject by intra-arterial, intravenous, intramuscular, subcutaneous or other parenteral administration, or potentially by oral administration for non-peptidergic inhibitors. Additionally or in lieu of post transplant administration, the subject may be treated with the C3b inhibitory agent prior to transplantation and/or during the transplant procedure, and/or by pretreating the organ or tissue to be transplanted with the C3b inhibitory agent. Pretreatment of the organ or tissue may include applying a solution, gel or paste containing the C3b inhibitory agent to the surface of the organ or tissue by spraying or irrigating the surface. The organ or tissue may also be soaked in a C3b inhibitor solution.

Central and Peripheral Nervous System Disorders and Injuries: Activation of the complement system has been implicated in the pathogenesis of a variety of central nervous system (CNS) or peripheral nervous system (PNS) diseases or injuries, including but not limited to multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD) and Alzheimer's disease (AD). It has now been shown that C3a receptors and C5a receptors are found on neurons and show widespread distribution in distinct portions of the sensory, motor, and limbic brain systems. The role of complement in CNS disorders has been identified by the initial determination that complement proteins are synthesized in CNS cells including neurons, astrocytes and microglia, as well as the realization that anaphylatoxins generated in the CNS following complement activation can alter neuronal function. Moreover, the anaphylatoxins C5a and C3a have been shown to alter eating and drinking behavior in rodents and can induce calcium signaling in microglia and neurons. These findings raise possibilities regarding the therapeutic utility of inhibiting complement activation in a variety of CNS inflammatory diseases including cerebral trauma, demyelination, meningitis, stroke, and Alzheimer's disease.

A common clinical problem is the occurrence of brain trauma or hemorrhage and activation of complement system may occur and worsen resulting inflammation and edema, which has led to the study of complement inhibition in a model of brain trauma in rats. Administration of sCR1 immediately prior to brain injury markedly inhibited neutrophil infiltration into the injured area, indicating complement was important for recruitment of phagocytic cells. Likewise, complement activation in patients following cerebral hemorrhage is clearly implicated by the presence of high levels of multiple complement activation products in both plasma and cerebrospinal fluid (CSF). Complement activation and increased staining of C5b-9 complexes have been demonstrated in sequestered lumbar disc tissue. This could suggest a role in disc herniation tissue-induced sciatica.

MS is characterized by a progressive loss of myelin ensheathing and insulating axons within the CNS, and although the initial cause is unknown, there is abundant evidence implicating the immune system. There is also clear evidence that complement plays a prominent role in the pathophysiology of CNS or PNS demyelinating diseases including MS, Guillain-Barre syndrome and Miller-Fisher syndrome. Despite clear evidence of complement involvement, the identification of complement therapeutic targets is only now being evaluated in experimental allergic encephalomyelitis (EAE), an animal model of multiple sclerosis. Complement contributes to tissue destruction, inflammation, clearance of myelin debris and even remyelination of axons. Studies have established that EAE mice deficient in C3 or factor B showed attenuated demyelination as compared, to EAE control mice. EAE mouse studies using a soluble form of a complement inhibitor coined "sCrry" and C3~/~ and factor B~/~ demonstrated that complement contributes to the development and progression of the disease model at several levels. In addition, the marked reduction in EAE severity in factor B~/~ mice provides further evidence for the role of the alternative pathway of complement in EAE.

MG is a disease of the neuromuscular junction with a loss of acetylcholine receptors and destruction of the end plate. The histological hallmarks of AD, a neurodegenerative disease, are senile plaques and neurofibrillary tangles. sCR1 is very effective in an animal model of MG, further indicating the role of complement in the disease. These pathological markers also stain strongly for components of the complement system. Evidence points to a local neuroinflammatory state that results in neuronal death and cognitive dysfunction. Senile plaques contain abnormal amyloid-.beta.-peptide (A.beta.), a peptide derived from amyloid precursor protein. A.beta. has been shown to bind C1 and can trigger complement activation. In addition, a prominent feature of AD is the association of activated proteins of the classical complement pathway from C1q to C5b-9, which have been found highly localized in the neuritic plaques. Thus, A.beta. initiates the classical pathway, as well as neuronal cell death due to a resulting continual inflammatory state. Moreover, the fact that complement activation in AD has progressed to the terminal C5b-9 phase indicates that the regulatory mechanisms of the complement system have been unable to halt the complement activation process.

Several inhibitors of the complement pathway have been proposed as potential therapeutic approaches for AD, including proteoglycan as inhibitors of C1Q binding, Nafamstat as an inhibitor of C3 convertase, and C5 activation blockers or inhibitors of C5a receptors. Supported by the wealth of data suggesting complement pathway involvement in AD, the role of C3b as an initiation step in the innate complement pathway, as well as for alternative pathway activation, provides a potential new therapeutic approach. In damaged regions in the brains of PD patients, as in other CNS degenerative diseases, there is evidence of inflammation characterized by glial reaction (especially microglia), as well as increased expression of HLA-DR antigens, cytokines, and components of complement. This raises strong suggestions that immune system mechanisms are involved in the pathogenesis of neuronal damage in PD. The cellular mechanisms of primary injury in PD have not been clarified, however, but it is likely that mitochondrial mutations, oxidative stress, and apoptosis play a role. In addition, it is found that neuronal damage initiated inflammation in the striatum and the substantial nigra in PD, has the capacity to aggravate the course of the disease. These observations suggest that treatment with complement inhibitory drugs may act to slow progression of PD.

One aspect of the invention is thus directed to a subject suffering from such a disorder or injury with a composition comprising a therapeutically effective amount of a C3b inhibitory agent in a pharmaceutical carrier can be receive treatment of peripheral nervous system (PNS) and/or central nervous system (CNS) disorders or injuries. CNS and PNS disorders and injuries that may be treated in accordance with the present invention are believed to include but are not limited to Miller-Fisher syndrome, multiple sclerosis (MS), Alzheimer's disease (AD), Parkinson's disease (PD myasthenia gravis (MG), Huntington's disease (HD), amyotrophic lateral sclerosis (ALS), Guillain Barre syndrome, reperfusion following stroke, degenerative discs, cerebral trauma), cerebral trauma and/or hemorrhage, demyelination and, possibly, meningitis.

For treatment of CNS conditions and cerebral trauma, the C3b inhibitory agent may be administered to the subject by intramuscular, intrathecal, intraventricular, intracranial, intra-arterial, subcutaneous, intravenous, or other parenteral administration, and potentially orally for non-peptidergic inhibitors. Treatment of PNS conditions and cerebral trauma may also include systemic administration or local administration to the site of dysfunction or trauma. Administration of the C3b inhibitory compositions of the present invention may be repeated periodically as determined by a physician until effective relief or control of the symptoms is achieved.

Blood Disorders

Sepsis is a serious condition in which there is an overwhelming reaction of the immune response to invading microorganisms. A major function of the complement system is to orchestrate the inflammatory response to invading bacteria and other pathogens, therefore it is thought to have a major role in the pathogenesis of sepsis, as has been shown in numerous studies. The definition of the clinical manifestations of sepsis is ever evolving. Sepsis is usually defined as the systemic host response to an infection. However, on many occasions in patients with septic symptoms, no clinical evidence for infection is found. This discrepancy was first taken into account at a Consensus Conference in 1992 when the term "systemic inflammatory response syndrome" (SIRS) was established, and for which no definable presence of bacterial infection was required. It is now generally agreed upon that sepsis and SIRS are accompanied by the regulation incapacity of the inflammatory response. For the purposes of this brief review, we will consider the clinical definition of sepsis to include severe sepsis, septic shock, and SIRS. The predominant source of infection in septic patients before the late 1980s was Gram-negative bacteria. The main component of the Gram-negative bacterial cell wall, Lipopolysaccharide (LPS), was known to motivate release of inflammatory mediators from various cell types and provoke acute infectious symptoms when injected into animals.

Interestingly, the spectrum of responsible microorganisms appears to have shifted from predominantly Gram-negative bacteria in the late 1970s and 1980s to predominantly Gram-positive bacteria at present, for reasons that are currently unclear. Numerous studies have illustrated the importance of complement activation in mediating inflammation as well as the contribution to the features of shock, particularly septic and hemorrhagic shock. Both Gram-negative and Gram-positive organisms commonly precipitate septic shock. The major components of the Gram-positive cell wall are peptidoglycan and lipoteichoic acid, and both components are potent activators of the alternative complement pathway, although in the presence of specific antibodies they can also activate the classical complement pathway.

The complement system was initially implicated in the pathogenesis of sepsis when it was noted by researchers that anaphylatoxins C3a and C5a mediate a variety of inflammatory reactions that might also occur during sepsis. These anaphylatoxins evoke vasodilation and an increase in microvascular permeability, events that play a central role in septic shock. In addition, the anaphylatoxins induce bronchospasm, histamine release from mast cells, and aggregation of platelets. Moreover, they exert numerous effects on granulocytes, such as adhesion, chemotaxis, aggregation, release of lysosomal enzymes, generation of toxic super oxide anion, and formation of leukotrienes. These biologic effects are thought to play a role in development of complications of sepsis such as shock or acute respiratory distress syndrome (ARDS). Furthermore, elevated levels of the anaphylatoxin C3a is associated with a fatal outcome in sepsis. Certain complement-deficient strains (e.g., C5-deficient ones) are more resistant to the effects of LPS infusions, in some animal models of shock.

The prevention of C5a generation with antibodies during the arrival of sepsis is rodents has been shown to greatly improve survival, while related findings were made when the C5a receptor (C5aR) was blocked, using either antibodies or a small molecular inhibitor. Despite earlier experimental studies in monkeys that suggested antibody blockade of C5a attenuated E. coli induced septic shock and adult respiratory distress syndrome. In humans with sepsis, when compared with that in less severely septic patients and survivors, C5a was elevated and associated with significantly reduced survival rates together with multi-organ failure. The mechanisms by which C5a exerts its harmful effects during sepsis are yet to be investigated in detail, but recent data suggests that the generation of C5a during sepsis significantly compromises innate immune functions of blood neutrophils, their ability to express a respiratory burst, and their ability to generate cytokines. In addition, C5a generation during sepsis appears to have procoagulant effects. The complement-modulating protein C1 INH has also shown efficacy in animal models of sepsis and ARDS.

The lectin pathway may also have a role in pathogenesis of sepsis. MBL has been shown to bind to a range of clinically important microorganisms including both Gram-negative and Gram-positive bacteria. MBL has also been shown to have the ability to activate the alternative pathway. Lipoteichoic acid (LTA) is increasingly regarded as the Gram-positive counterpart of LPS and is a potent immunostimulant that induces cytokine release from mononuclear phagocytes and whole blood.

An aspect of the invention thus provides a method for treating sepsis or a condition resulting from sepsis. It is possible to administer a composition comprising a therapeutically effective amount of a C3b inhibitory agent in a pharmaceutical carrier to a subject suffering from sepsis or a condition resulting from sepsis including without limitation severe sepsis, septic shock, acute respiratory distress syndrome resulting from sepsis, and systemic inflammatory response syndrome. Related methods are provided for the treatment of other blood disorders, including hemorrhagic shock, autoimmune thrombotic thrombocytopenic purpura (TTP), hemolytic anemia, hemolytic uremic syndrome (HUS) or other marrow/blood destructive conditions, by administering a composition comprising a therapeutically effective amount of a C3b inhibitory agent in a pharmaceutical carrier to a subject suffering from such a condition. The C3b inhibitory agent, is administered to the subject systemically, such as by intra-arterial, intravenous, intramuscular, inhalational (particularly in the case of ARDS), subcutaneous or other parenteral administration, or potentially by oral administration for non-peptidergic agents. Combination is possible of the C3b inhibitory agent composition with one or more additional therapeutic agents to combat the sequelae of sepsis and/or shock. For advanced sepsis or shock or a distress condition resulting from, the C3b inhibitory composition may suitably be administered in a fast-acting dosage form, such as by intravenous or infra-arterial delivery of a bolus of a solution containing the C3b inhibitory agent composition. Repetitive administration of the agent may be necessary until the condition has been resolved, as determined by a physician.

Urogenital Conditions

The complement system has been implicated in several distinct urogenital disorders including painful bladder disease, sensory bladder disease, chronic abacterial cystitis and interstitial cystitis, infertility, pregnancy, fetomaternal tolerance, and pre-eclampsia.

Sensory bladder disease, painful bladder disease, chronic abacterial cystitis and interstitial cystitis are ill-defined conditions of unknown etiology and pathogenesis, and, therefore, they are without any rational therapy. The dominating pathogenetic theories often concern defects in the epithelium and/or mucous surface coating of the bladder, as well as immunological disturbances. Patients with interstitial cystitis were reported to have been tested for immunoglobulin (IgA, G, M), complement components (C1q, C3, C4), and C1-esterase inhibitor. Resulting in findings that immunoglobulin G was markedly elevated (p less than 0.001) and a significant depletion of serum levels of complement component C4 (p less than 0.001). This study suggests classical pathway activation of the complement system, and supports the possibility that a chronic local immunological process is involved in the pathogenesis of the disease. Moreover, following binding of autoantibodies to antigens in bladder mucosa, activation of complement could be involved in the production of tissue injury and in the chronic self-perpetuating inflammation typical of this disease.

In addition to the role of complement in urogenital inflammatory diseases, reproductive functions may be impacted by the local regulation of the complement pathway. Naturally occurring complement inhibitors have evolved to provide host cells with the protection they need to control the body's complement system. A naturally occurring rodent complement inhibitor that is structurally similar to the human complement inhibitors, MCP and DAF, called Crry, has been investigated to delineate the regulatory control of complement in fetal development. Interestingly, attempts to generate Crry~/~ mice were unsuccessful. Instead, it was discovered that homozygous Crry~/~ mice died in utero. Crry~/~ embryos survived until about 10 days post coitus, and survival rapidly declined with death resulting from developmental arrest. There was also a marked invasion of inflammatory cells into the placental tissue of Crry~/~ embryos. In contrast, Crry+/+ embryos appeared to have C3 deposited on the placenta. This deposition suggests that complement activation occurred at the placenta level. In the absence of complement regulation, the embryos died. Confirming studies investigated the introduction of the Crry mutation onto a C3 deficient background, which was successful. Together, these data illustrate that the fetomaternal complement interface must be regulated. Subtle alterations in complement regulation within the placenta might contribute to placental dysfunction and miscarriage.

Pre-eclampsia is a pregnancy-induced hypertensive disorder in which complement system activation has been implicated but remains controversial. Even though no elevations were seen prior to the presence of clinical symptoms, complement activation in systemic circulation is closely related to established disease in pre-eclampsia, therefore, complement components cannot be used as predictors of pre-eclampsia. However, increased complement activation at the local environment of the placenta bed might overcome local control mechanisms, resulting in raised levels of anaphylatoxins and C5b-9.

One proposed mechanism of infertility related to antisperm antibodies (ASA) is through the role of complement activation in the genital tract. Elevated C5b-9 levels have been demonstrated in ovarian follicular fluid of infertile women. Generation of C3b and iC3b opsonin, which can potentiate the binding of sperm by phagocytic cells via their complement receptors as well as formation of the terminal C5b-9 complex on the sperm surface, thereby reducing sperm motility, are potential causes associated with reduced fertility. Other studies have shown impairment in sperm migration, and reduced sperm/egg interactions, which may be complement associated. Finally, studies with sCR1 demonstrated a protective effect against ASA- and complement mediated injury to human sperm. These data provide several lines of evidence for the use of complement inhibitors in the treatment of urogenital disease and disorders.

Provided is a method for inhibiting C3b-dependent complement activation in a patient suffering from a urogenital disorder as an aspect of the invention. Done by administering a composition comprising a therapeutically effective amount of a C3b inhibitory agent in a pharmaceutical carrier. Some of the urogenital disorders thought to be subject to treatment with the methods and compositions related to the present invention include but are not limited to, sensory bladder disease, painful bladder disease, chronic abacterial cystitis and interstitial cystitis, male and female infertility, placental dysfunction and miscarriage and pre-eclampsia. The C3b inhibitory composition may be delivered locally to the urogenital tract, such as by intravesical irrigation or instillation with a liquid solution or gel composition. Alternatively, the C3b inhibitory agent may be administered to the subject systemically, such as by intra-arterial, intravenous, intramuscular, inhalational, subcutaneous or other parenteral administration, or potentially by oral administration for non-peptidergic agents. Repeated administration may be carried out as determined by a physician to control or resolve the condition.

Diabetes and Diabetic Conditions

Complement system activation can cause increased permeability, leukostasis, microthrombosis, and apoptosis of capillary cells, all of which are characteristic of diabetic retinal microangiopathy. Glomerular structures and endoneurial microvessels of patients with diabetes show signs of complement activation. Decreased availability or effectiveness of complement inhibitors in diabetes has been suggested by the findings that high glucose in vitro selectively decreases on the endothelial cell surface the expression of CD55 and CD59, the two inhibitors that are glycosylphosphatidylinositol (GPI)-anchored membrane proteins, and that CD59 undergoes nonenzymatic glycation that hinders its complement-inhibitory function.

Studies by Zhang et al., investigated complement activation and the association with changes in inhibitory molecules as well as a feature of human nonproliferative diabetic retinopathy. Deposition of C5b-9, the terminal product of complement activation, was found to occur in the wall of retinal vessels of human eye donors with type-2 diabetes, but not in the vessels of age-matched nondiabetic donors. C1q and C4, the complement components unique to the classical pathway were not found in the diabetic retinas, which indicate that C5b-9 was generated via the alternative pathway. In the diabetic donors the retinal levels of CD55 and CD59, the two complement inhibitors linked to the plasma membrane by GPI anchors were found to be dramatically reduced. Similar complement activation in retinal vessels and selective reduction in the levels of retinal CD55 and CD59 were observed in rats with a 10-week duration of streptozotocin-induced diabetes. Thus, diabetes appears to cause defective regulation of complement inhibitors and complement activation that precede most other manifestations of diabetic retinal microangiopathy. Gerl et al. determined the presence of activated complement components in eyes affected by diabetic retinopathy.

Extensive deposits of complement C5b-9 complexes were detected in the choriocapillaris immediately underlying the Bruch membrane and densely surrounding the capillaries in all 50 diabetic retinopathy specimens following immunohistochemical study. Staining for C3d positively correlated with C5b-9 staining, indicative of the fact that complement activation had occurred in situ. Furthermore, positive staining was found for vitronectin, which forms stable complexes with extracellular C5b-9. In contrast, there was no positive staining for C-reactive protein (CRP), mannan-binding lectin (MBL), C1q, or C4, indicating that complement activation did not occur through a C4-dependent pathway. Thus, there are indications that the presence of C3d, C5b-9, and vitronectin illustrate complement activation completion occurs through the alternative pathway in the choriocapillaris of eyes affected by diabetic retinopathy. Complement activation may be a causative factor in the pathologic sequelae that can contribute to ocular tissue disease and visual impairment. Therefore, the use of a complement inhibitor may be an effective therapy to reduce or block damage to microvessels that occurs in diabetes.

Insulin dependent diabetes mellitus (IDDM, also referred to as Type-I diabetes) is an autoimmune disease associated with the presence of different types of autoantibodies. The presence of these antibodies and the corresponding antigens, which are known to persist in the blood for long periods, leads to the formation of circulating immune complexes (CIC). Deposition of CIC in the small blood vessels has the potential to lead to microangiopathy with debilitating clinical consequences. A correlation exists between CIC and the development of microvascular complications in diabetic children and findings suggest that elevated levels of CIC IgG are associated with the development of early diabetic nephropathy and that an inhibitor of the complement pathway may be effective at blocking diabetic nephropathy. In addition, the formation of downstream complement proteins and the involvement of the alternative pathway are likely to be a contributory factor in overall islet cell function in IDDM and the use of a complement inhibitor to reduce potential damage or limit cell death is expected.

Methods are provided in another aspect of the invention, for inhibiting C3b-dependent complement activation in a subject suffering from non-obese diabetes (IDDM) or from angiopathy, neuropathy or retinopathy complications of IDDM or adult onset (Type-2) diabetes, by administering a composition comprising a therapeutically effective amount of a C3b inhibitor in a pharmaceutical carrier. There is also the option of administering the C3b inhibitory to the subject systemically, such as by intra-arterial, intravenous, intramuscular, subcutaneous or other parenteral administration, or potentially by oral administration for non-peptidergic agents. Alternatively, administration may be by local delivery to the site of angiopathic, neuropathic or retinopathic symptoms. The C3b inhibitory agent could also be administered periodically over an extended period for treatment or control of a chronic condition, or by a single or series of administrations for treatment of an acute condition.

Perichemotherapeutic Administration and Treatment of Malignancies:

Activation of the complement system may also be implicated in the pathogenesis of malignancies. Recently, the neoantigens of the C5b-9 complement complex, IgG, C3, C4, S-protein/vitronectin, fibronectin, and macrophages were localized on breast cancer using polyclonal or monoclonal antibodies and the streptavidin-biotin-peroxidase technique. All the tissue samples with carcinoma in each the TNM stages presented C5b-9 deposits on the membranes of tumor cells, thin granules on cell remnants, and diffuse deposits in the necrotic areas. In addition, complement activation may be a consequence of chemotherapy or radiation therapy and thus inhibition of complement activation would be useful as an adjunct in the treatment of malignancies to reduce iatrogenic inflammation. C5b-9 deposits were more intense and extended when chemotherapy and radiation therapy preceded surgery. The C5b-9 deposits were absent in all the samples with benign lesions. S-protein/vitronectin was present as fibrillar deposits in the connective tissue matrix and as diffuse deposits around the tumor cells, less intense and extended than fibronectin. IgG, C3, and C4 deposits were present only in carcinoma samples. The presence of C5b-9 deposits is indicative of complement activation and its subsequent pathogenetic effects in breast cancer. Pulsed tunable dye laser (577 nm) (PTDL) therapy induces hemoglobin coagulation and tissue necrosis, which is mainly limited to blood vessels.

In a PTDL-irradiated normal skin study, the main findings were as follows:

1. C3 fragments, C8, C9, and MAC were deposited in vessel walls

2. Deposits were not due to denaturation of the proteins since they became apparent only 7 min after irradiation, contrary to immediate deposition of transferrin at the sites of erythrocyte coagulates 3. C3 deposits were shown to amplify complement activation by the alternative pathway, a reaction which was specific since tissue necrosis itself did not lead to such amplification 4. These reactions preceded the local accumulation of polymorphonuclear leucocytes.

Tissue necrosis was more pronounced in the hemangiomas. The larger angiomatous vessels in the center of the necrosis did not fix complement significantly. By contrast, complement deposition in the vessels situated at the periphery was similar to that observed in normal skin with one exception: C8, C9, and MAC were detected in some blood vessels immediately after laser treatment, a finding consistent with assembly of the MAC occurring directly without the formation of a C5 convertase. These results indicate that complement is activated in PTDL-induced vascular necrosis, and might be responsible for the ensuing inflammatory response.

Photodynamic therapy (PDT) of tumors elicits a strong host immune response, and one of its manifestations is a pronounced neutrophilia. In addition to complement fragments (direct mediators) released because of PDT-induced complement activation, there are at least a dozen secondary mediators that all arise because of complement activity. The latter include cytokines IL-1beta, TNF-alpha, IL-6, IL-10, G-CSF and KC, thromboxane, prostaglandins, leukotrienes, histamine, and coagulation factors.

Finally, in conjunction with the standard therapeutic regimen for the treatment of cancer, the use of inhibitors of C3b-dependent complement activation may be added. For example, treatment with rituximab, a chimeric anti-CD20 monoclonal antibody is known to cause moderate to severe first-dose side effects, mostly in patients with high numbers of circulating tumor cells. Recent studies during the first infusion of rituximab measured complement activation products (C3b/c and C4b/c) and cytokines (tumor necrosis factor alpha (TNF-alpha), interleukin 6 (IL-6) and IL-8) in five relapsed low-grade non-Hodgkin's lymphoma (NHL) patients. Infusion of rituximab induced rapid complement activation, preceding the release of TNF-alpha, IL-6 and IL-8. Although the study group was small, the level of complement activation appeared to be correlated both with the number of circulating B cells prior to the infusion (r=0.85; P=0.07), and with the severity of the side effects. The results indicated that complement plays a pivotal role in the pathogenesis of side effects of rituximab treatment. As complement activation cannot be prevented by corticosteroids, it may be relevant to study the possible role of complement inhibitors during the first administration of rituximab.

In another aspect of the invention, methods are provided for inhibiting C3b-dependent complement activation in a subject being treated with chemotherapeutics and/or radiation therapy, including without limitation for the treatment of cancerous conditions. This method includes administering a composition comprising a therapeutically effective amount of a C3b inhibitor in a pharmaceutical carrier to a patient perichemotherapeutically, i.e., before and/or during and/or after the administration of chemotherapeutic(s) and/or radiation therapy. For example, administration of a C3b inhibitor composition may be commenced before or concurrently with chemo- or radiation therapy, and continued throughout the course or following the therapy. This could be used to reduce the detrimental effects of the chemo- and/or radiation therapy in the non-targeted, healthy tissues. It is understood that chemo- and radiation therapy regimens often entail repeated treatments and, therefore, it is possible that administration of a C3b inhibitor composition would also be repetitive and relatively coincident with the chemotherapeutic and radiation treatments. It is also believed that C3b inhibitory agents may be used as chemotherapeutic agents, alone or in combination with other chemotherapeutic agents and/or radiation therapy, to treat patients suffering from malignancies. Suitable administration may be via oral (for non-peptidergic), intravenous, intramuscular, or other parenteral route.

Endocrine Disorders

The complement system has also been recently associated with a few endocrine conditions or disorders including Hashimoto's thyroiditis, stress, anxiety and other potential hormonal disorders involving regulated release of prolactin, growth or insulin-like growth factor, and adrenocorticotropin from the pituitary Ophthalmologic Conditions Age-related macular degeneration (AMD) is a blinding disease that afflicts millions of adults, and results in the progressive destruction of the macula that has been correlated with the formation of extracellular deposits called drusen located in and around the macula, behind the retina and between the retina pigment epithelium (RPE) and the choroid. Recent studies have revealed that prevalent among drusen-associated individuals are proteins associated with inflammation and immune-mediated processes. Transcripts that encode a number of these molecules have been detected in retinal, RPE, and choroidal cells. This data also demonstrates that dendritic cells, which are potent antigen-presenting cells, are intimately associated with drusen development, and that complement activation is a key pathway that is active both within drusen and along the RPE-choroid interface.

Strong association between AMD and a genetic polymorphism, has been found by numerous independent studies, in the gene for complement factor H (CFH) in which the likelihood of AMD is increased by a factor of 7.4 in individuals homozygous for the risk allele. The CFH gene has been mapped to chromosome 1q31 a region that had been implicated in AMD by six independent linkage scans (see, e.g., D. W. Schultz et al). CFH is known to be a key regulator of the complement system. It has been shown that CFH on cells and in circulation regulates complement activity by inhibiting the activation of C3 to C3a and C3b, and by inactivating existing C3b. Deposition of C5b-9 has been observed in Brusch's membrane, the intercapillary pillars and within drusen in patients with AMD. Immunofluorescence experiments suggest that in AMD, the polymorphism of CFH may give rise to complement deposition in chorodial capillaries and chorodial vessels.

The membrane-associated complement inhibitor, complement receptor 1, is also localized in drusen, but it is not detected in RPE cells immunohistochemically. In contrast, a second membrane-associated complement inhibitor, membrane cofactor protein, is present in drusen-associated RPE cells, as well as in small, spherical substructural elements within drusen. These previously unidentified elements also show strong immunoreactivity for proteolytic fragments of complement component C3 that are characteristically deposited at sites of complement activation. It is proposed that these structures represent residual debris from degenerating RPE cells that are the targets of complement attack.

An aspect of the invention thus provides a method for inhibiting C3b-dependent complement activation to treat age-related macular degeneration or other complement mediated ophthalmologic condition by administering a composition comprising a therapeutically effective amount of a C3b inhibitory agent in a pharmaceutical carrier to a subject suffering from such a condition or other complement-mediated ophthalmologic condition. The C3b inhibitory composition may be administered locally to the eye, such as by irrigation or application of the composition in the form of a gel, salve or drops. Alternately, the C3b inhibitory agent may be administered to the subject systemically, such as by intra-arterial, intravenous, intramuscular, inhalational, nasal, subcutaneous or other parenteral administration, or potentially by oral administration for non-peptidergic agents. The C3b inhibitory agent composition may be combined with one or more additional therapeutic agents. Administration may be repeated as determined by a physician until the condition has been resolved or is controlled.

C3b Inhibitory Agents

In one aspect, the present invention provides methods of inhibiting the adverse effects of C3b-dependent complement activation. C3b inhibitory agents are administered in an amount effective to inhibit C3b-dependent complement activation in a living subject. In the practice of this aspect of the invention, representative C3b inhibitory agents include anti-C3b antibodies that prevent binding of C3b to properdin or factor B, and prevent production of C3a, C5a and C5b-9 by inhibition of the C3 cleavage into C3b. The C3b inhibitory agents can be used alone as a primary therapy or in combination with other methods as complement to enhance the benefits of other treatments.

There are certain items characteristic of the inhibition of C3b-dependent complement activation that occurs from administration of a C3b inhibitory agent in accordance with the methods of the invention. These include the reduction of C3 cleavage and C3b deposition, the inhibition of production of complement activation products C3a, C5a and/or C5b-9 (MAC), and the reduction of alternative complement activation assessed in a hemolytic assay using un-sensitized rabbit or guinea pig red blood cells. According to the present invention, C3b inhibitory agents utilized are effective in inhibiting the C3b-dependent complement activation system, possibly by blocking the biological function of C3b.

Anti-C3b Antibodies

In some aspects of the invention, the C3b inhibitory agent comprises an anti-C3b antibody that inhibits the C3b-dependent complement activation system including polyclonal, monoclonal or recombinant antibodies derived from any antibody-producing mammal and may be multispecific, chimeric, humanized, anti-idiotype, and antibody fragments. Antibody fragments include Fab, Fab', F(ab).sub.2, F(ab').sub.2, Fv fragments, scFv fragments and single-chain antibodies as further described herein.

The described assays were used to screen several anti-C3b antibodies described in the literature, for inhibition ability of the C3b-dependent complement activation system. Upon identifying inhibitory abilities of an anti-C3b antibody, it can be used to produce anti-idiotype antibodies as well as identify other C3b binding molecules and Anti-C3b Antibodies with reduced effector function. IgG molecules in which the Fc portion of the molecule has been removed by enzymatic cleavage are devoid of this effector function (see Harlow, Antibodies: A Laboratory Manual, Cold Spring Harbor Laboratory, New York, 1988). By having a genetically engineered Fc sequence that minimizes effector function, or being of either the human $IgG_2$ or $IgG_4$ isotype, antibodies with reduced effector function are able to be generated as the result of lacking the Fc portion of the molecule.

Antibodies with reduced effector function can be produced by standard molecular biological manipulation of the Fc portion of the IgG heavy chains as described in Jolliffe, et al., and Rodrigues, et al. Antibodies with reduced effector function also include IgG2 and IgG4 isotypes that have a reduced ability to activate complement and/or interact with Fc receptors. Humanized or fully human antibodies specific to human C3b comprised of IgG2 or IgG4 isotypes can be produced by one of several methods known to one of ordinary skilled in the art, as described in Vaughan, T. J., et al.

Production of Anti-C3b Antibodies

Production of anti-C3b antibodies can be completed by utilizing C3, C3b, C3b polypeptides or using antigenic C3b epitope-bearing peptides (e.g., a portion of the C3b polypeptide). It is possible to isolate the C3b peptides and polypeptides used to raise antibodies as natural polypeptides, recombinant or synthetic peptides, and catalytically inactive recombinant polypeptides. This aspect of the invention provides anti-C3b antibodies obtained using a transgenic mouse strain. Antigens useful for producing anti-C3b antibodies also include fusion polypeptides.

Polyclonal Antibodies

Using well-known methods, polyclonal antibodies against C3b can be prepared by immunizing an animal with C3b polypeptide or an immunogenic portion thereof. The immunogenicity of a C3b polypeptide can be increased through the use of an adjuvant, including mineral gels, such as aluminum hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as dogs, goats, chickens, rats, mice, horses, cows, rabbits, guinea pigs, or sheep. Alternatively, an anti-C3b antibody useful in the present invention may also be derived from a subhuman primate. Sera containing immunologically active antibodies are then produced from the blood of such immunized animals using standard procedures.

Monoclonal Antibodies

In some embodiments, the C3b inhibitory agent is a highly specific anti-C3b monoclonal antibody being directed against a single C3b epitope. As used herein, the modifier "monoclonal" indicates the character of the antibody as being obtained from a substantially homogenous population of antibodies, and should not be considered to require production by any particular method. Monoclonal antibodies can be obtained using any technique that provides for the production of antibody molecules by continuous cell lines in culture, such as the hybridoma method described by Kohler, G., et al., or they may be made by recombinant DNA methods. It is also possible to isolate monoclonal antibodies from phage antibody libraries using the techniques described in Clackson, T., et al., and Marks, J. D., et al. Such antibodies can be of any immunoglobulin class including IgG, IgM, IgE, IgA, IgD and any subclass thereof. For example, monoclonal antibodies can be obtained by injecting a suitable mammal with a composition comprising a C3b polypeptide or portion thereof. After a predetermined period, splenocytes are removed from the mammal and suspended in a cell culture medium. The splenocytes are then fused with an immortal cell line to form a hybridoma. The formed hybridomas are grown in cell culture and screened for their ability to produce a monoclonal antibody against C3b.

Human-monoclonal antibodies may be obtained using transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice have the ability to synthesize human antibodies specific for human antigens, such as the C3b antigens described herein. The mice can also be used to produce human C3b antibody-secreting hybridomas by fusing B-cells from such animals to suitable myeloma cell lines using conventional Kohler-Milstein technology as further described in Example 7. Transgenic mice with a human immunoglobulin genome are commercially available. Methods for obtaining human antibodies from transgenic mice are described, for example, by Green, L. L., et al; Lonberg, N., et al.; and Taylor, L. D., et al.

Monoclonal antibodies can be isolated and purified from hybridoma cultures by a variety of well-established techniques that include affinity chromatography with Protein-A Sepharose, size-exclusion chromatography, and ion-exchange chromatography (see, for example, Coligan; Baines et al.).

Once produced, polyclonal, monoclonal, or phage-derived antibodies are first tested for specific C3b binding. A variety of assays known to those skilled in the art may be utilized to detect antibodies that specifically bind to C3b. Examples of assays include western blot or immunoprecipitation analysis by standard methods (e.g., as described in Ausubel et al.), immunoelectrophoresis, enzyme-linked immuno-sorbent assays, dot blots, inhibition or competition assays and sandwich assays as described in Harlow and Land, Antibodies: A Laboratory Manual. Once antibodies are identified that specifically bind to C3b, the anti-C3b antibodies are tested for the ability to function as a C3b inhibitory agent in one of several assays such as a rabbit erythrocyte hemolysis assay for alternative pathway activation, sensitized sheep erythrocyte for classical pathway activation assay, C3b deposition assay, C3a and C5a productions assays. The affinity of anti-C3b monoclonal antibodies can be readily determined by one of ordinary skill in the art (see, e.g., Scatchard, A.). In one embodiment, the anti-C3b monoclonal antibodies useful for the methods of the invention bind to C3b with a binding affinity of <100 nM, preferably <10 nM and most preferably <2 nM.

By way of example, monoclonal antibodies that bind to C3b were obtained from Quidel Corporation (San Diego, Calif.) and screened or assayed as described in the Examples for their ability to inhibit binding of C3b to properdin or factor B, and/or prevent production of C3a, C5a and C5b-9 by inhibition of the C3b function. One of the monoclonal antibodies identified as Catalog No. A205, Lot No. A205B22701 as shown in the Examples was found to inhibit binding of C3b to factor B, inhibit alternative pathway dependent hemolysis of rabbit erythrocytes and abrogate the effects of the alternative complement pathway.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass. While the remainder of the chain(s) is identical with or homologous to corresponding sequences in antibodies derived from another species or belonging to another antibody class or subclass, as well as fragments of such antibodies. One form of a chimeric antibody useful in the invention is a humanized monoclonal anti-C3b antibody. Chimeric antibodies are humanized forms of non-human (e.g., murine) antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to refine antibody performance. In general, the humanized antibody will comprise substantially of at least one, and typically two variable domains, in which all or virtually all of the hyper variable loops correspond to those of a non-human immunoglobulin and all or substantially all of the Fv framework regions are those of a human immunoglobulin sequence.

The humanized antibody optionally also will comprise at least a portion of an immunoglobulin constant region (Fc), typically that of a human immunoglobulin. For further details, see Jones, P. T., et al.; Reichmann, L., et al. The humanized antibodies useful in the invention include human monoclonal antibodies including at least a C3b binding CDR3 region. In addition, the Fc portions may be replaced to produce IgA or IgM as well as human IgG antibodies. Such humanized antibodies will have particular clinical utility because they will specifically recognize human C3b but will not evoke an immune response in humans against the antibody itself. Consequently, they are better suited for in vivo administration in humans, especially when repeated or long-term administration is necessary. Techniques for producing humanized monoclonal antibodies are described, by, "Engineering Therapeutic Antibodies," in Protein Engineering: Principles and Practice; and by U.S. Pat. No. 5,693,762. In addition, there are commercial entities that will synthesize humanized antibodies from specific murine antibody regions, such as Protein Design Labs (Mountain View, Calif.), Medarex and Xoma.

Recombinant Antibodies

Anti-C3b antibodies can also be made using recombinant methods. For example, human antibodies can be made using human immunoglobulin expression libraries (available for example, from Stratagene, Corp., La Jolla, Calif.) to produce fragments of human antibodies ($V_H$, $V_L$, Fv, Fd, Fab or $F(ab')_2$), which are then used to construct whole human antibodies using techniques similar to those for producing chimeric antibodies.

Anti-Idiotype Antibodies

Once anti-C3b antibodies are identified with the desired inhibitory activity, these antibodies can be used to generate anti-idiotype antibodies that resemble a portion of C3b using techniques that are well known in the art. See, e.g., Greenspan, N. S., et al., FASEB J. 7:437, 1993. For example, antibodies that bind to C3b and competitively inhibit a C3b protein interaction required for complement activation can be used to generate anti-idiotypes that resemble the C3b binding site on C3b protein and therefore bind and neutralize a binding ligand of C3b.

Immunoglobulin Fragments

The C3b inhibitory agents useful in the method of the invention encompass intact immunoglobulin molecules as well as the relatively well known fragments including Fab, Fab', $F(ab)_2$, $F(ab')_2$ and Fv fragments, scFv fragments, diabodies, linear antibodies, single-chain antibody molecules and multispecific antibodies formed from antibody fragments. It is well known in the art that only a small portion of an antibody molecule, the paratope, is involved in the binding of the antibody to its epitope. The pFc' and Fc regions of the antibody are effectors of the classical complement pathway, but are not involved in antigen binding. An antibody from which the pFc' region has been enzymatically cleaved, or which has been produced without the pFc' region, is designated an $F(ab')_2$ fragment and retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Proteolytic hydrolysis, such as by pepsin or papain digestion of whole antibodies by conventional methods can obtain antibody fragments. For example, antibody fragments can be produced by enzymatic cleavage of antibodies with pepsin to provide $F(ab')_2$. This fragment can be further cleaved using a thiol reducing agent to produce Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331, Porter, R. R; Edelman, et al.; and by Coligan at pages 2.8.1-2.8.10 and 2.10.-2.10.4.

In some embodiments, the use of antibody fragments lacking the Fc region are preferred to avoid activation of the classical complement pathway, which is initiated upon binding Fc to the Fc.gamma. receptor. One can produce a MoAb that avoids Fcγ receptor interactions by several methods. For example, the Fc region of a monoclonal antibody can be removed chemically using partial digestion by proteolytic enzymes (such as ficin digestion), thereby generating, for example, antigen-binding antibody fragments such as Fab or F(ab)$_2$ fragments. Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for C3b in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described for example, by Whitlow, et al; Bird, et al.; U.S. Pat. No. 4,946,778; Pack, P., et al.

As an illustrative example, a C3b specific scFv can be obtained by exposing lymphocytes to C3b polypeptide in vitro and selecting antibody display libraries in phage or similar vectors (for example, using immobilized or labeled C3b protein or peptide). Genes encoding polypeptides having potential C3b polypeptide-binding domains can be obtained by screening random peptide libraries displayed on phage or on bacteria such as *E. coli*. These random peptide display libraries can be used to screen for peptides that interact with C3b. Techniques for creating and screening such random peptide display libraries are well known in the art and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). The C3b antibodies described herein are administered to a subject in need thereof to inhibit C3b-dependent complement activation. In some embodiments, the C3b inhibitory agent is a high-affinity human or humanized or chimeric monoclonal anti-C3b antibody with reduced effector function.

Additional Agents

The compositions and methods comprising C3b inhibitory agents may optionally comprise one or more additional therapeutic agents. These may augment the activity of the C3b inhibitory agent or that provide related therapeutic functions in an additive or synergistic fashion. For example, one or more C3b inhibitory agents may be administered in combination with one or more anti-inflammatory and/or analgesic agents. The inclusion and selection of additional agent(s) will be determined to achieve a desired therapeutic result. Suitable anti-inflammatory and/or analgesic agents include: serotonin receptor agonists; interleukin receptor antagonists; histamine receptor antagonists: serotonin receptor antagonists; bradykinin receptor antagonists; kallikrein inhibitors; tachykinin receptor antagonists, including neurokinin, and neurokinin-.sub.2 receptor subtype antagonists; calcitonin gene-related peptide (CGRP) receptor antagonists; inhibitors of enzymes active in the synthetic pathway for arachidonic acid metabolites, including phospholipase inhibitors, including PLA-.sub.2 isoform inhibitors and PLC.sub..gamma. isoform inhibitors, cyclooxygenase (COX) inhibitors (which may be either COX-1, COX-2 or nonselective COX-1 and -2 inhibitors), lipoxygenase inhibitors; prostanoid receptor antagonists including eicosanoid EP-1 and EP-4 receptor subtype antagonists and thromboxane receptor subtype antagonists; leukotriene receptor antagonists including leukotriene B.sub.4 receptor subtype antagonists and leukotriene D.sub.4 receptor subtype antagonists; opioid receptor agonists, including .mu.-oploid, .delta.-opioid, and .kappa.-opioid receptor subtype agonists; purinoceptor agonists and antagonists including P2X receptor antagonists and P$_2$Y receptor agonists; adenosine triphosphate (ATP)-sensitive potassium channel openers; MAP kinase inhibitors; nicotinic acetylcholine inhibitors; and alpha adrenergic receptor agonists (including alpha-1, alpha-2 and nonselective alpha-1 and 2 agonists).

The C3b inhibitory agent of the present invention, when used in the prevention or treatment of restenosis may be combined with one or more anti-restenosis agents for concomitant administration. Suitable anti-restenosis agents include: antiplatelet agents including: thrombin inhibitors and receptor antagonists, adenosine diphosphate (ADP) receptor antagonists (also known as purinoceptor receptor antagonists), thromboxane inhibitors and receptor antagonists and platelet membrane glycoprotein receptor antagonists; inhibitors of cell adhesion molecules, including selectin inhibitors and integrin inhibitors; anti-chemotactic agents; interleukin receptor antagonists; and intracellular signaling inhibitors including: protein kinase C (PKC) inhibitors and protein tyrosine phosphatases, modulators of intracellular protein tyrosine kinase inhibitors, inhibitors of src homology.sub.2 (SH2) domains, and calcium channel antagonists.

The C3b inhibitory agents of the present invention may also be administered in combination with one or more other complement inhibitors. No complement inhibitors are currently approved for use in humans, however some pharmacological agents have been shown to block complement in vivo. Many of these agents are also toxic or are only partial inhibitors, and use of these has been limited to use as research tools. K76COOH and nafamstat mesilate are two agents that have shown some effectiveness in animal models of transplantation. Low molecular weight heparins have also been shown to be effective in regulating complement activity. It is believed that these small molecule inhibitors may be useful as agents to use in combination with the C3b inhibitory agents of the present invention.

When used in the treatment of arthritides (e.g., osteoarthritis and rheumatoid arthritis), the C3b inhibitory agent of the present invention may be combined with one or more chondroprotective agents, which may include one or more promoters of cartilage anabolism and/or one or more inhibitors of cartilage catabolism, and suitably both an anabolic agent and a catabolic inhibitory agent, for concomitant administration. Suitable anabolic promoting chondroprotective agents include interleukin (IL) receptor agonists including IL-4, IL-10, IL-13, rhIL-4, rhIL-10 and rhIL-13, and chimeric IL-4, IL-10 or IL-13; Transforming growth factor-.beta. superfamily agonists, including TGF-β, TGF-β1, TGF-β2, TGF-β3, bone morphogenic proteins including BMP-2, BMP-4, BMP-5, BMP-6, BMP-7 (OP-1), and OP-2/BMP-8, growth-differentiation factors including GDF-5, GDF-6 and GDF-7, recombinant TGF-μs and BMPs, and chimeric TGF-βs and BMPs; insulin-like growth factors including IGF-1; and fibroblast growth factors including bFGF. Suitable catabolic inhibitory chondroprotective agents include Interleukin-1 (IL-1) receptor antagonists (IL-1ra), including soluble human IL-1 receptors (shuIL-1R), rshuIL-1R, rhIL-1ra, anti-1L1-antibody, AF11567, and AF12198; Tumor Necrosis Factor (TNF) Receptor Antagonists (TNF-.alpha.), including soluble receptors including sTNFRI and sTNFRII, recombinant TNF soluble receptors, and chimeric TNF soluble receptors including chimeric rhTNFR:Fc, Fc fusion soluble receptors and anti-TNF antibodies; cyclooxygenase-2 (COX-2 specific) inhibitors, including DuP 697, SC-58451, celecoxib, rofecoxib, nimesulide, diclofenac, meloxicam, piroxicam, NS-398, RS-57067, SC-57666, SC-58125, flosulide, etodolac, L-745,337 and DFU-T-614; Mitogen-activated protein kinase (MAPK) inhibitors, including inhibitors of ERK1, ERK2, SAPK1, SAPK2a, SAPK2b, SAPK2d, SAPK3, including SB 203580, SB 203580 iodo, SB202190, SB 242235, SB 220025, RWJ 67657, RWJ 68354, FR 133605, L-167307, PD 98059, PD 169316; inhibitors of nuclear factor kappa B (NF.kappa.B), including caffeic acid phenylethyl ester (CAPE), DM-CAPE, SN-50 peptide, hymenialdisine and pyrrolidone dithiocarbamate; nitric oxide synthase (NOS) inhibitors, including N.sup.G-monomethyl-L-arginine, 1400W, diphenyleneiodium, S-methyl isothiourea, S-(aminoethyl)isothiourea, L-N.sup.6-(1-iminoethyl)lysine, 1,3-PBITU, 2-ethyl-2-thiopseudourea, aminoguanidine, N.sup..omega.-nitro-L-arginine, and N.sup..omega.-nitro-L-arginine methyl ester, inhibitors of matrix metalloproteinases (MMPs), including inhibitors of MMP-1, MMP-2, MMP-3, MMP-7, MMP-8, MMP-9, MMP-10, MMP-11, MMP-12, MMP-13, MMP-14 and MMP-15, and including U-24522, minocycline, 4-Abz-Gly-Pro-D-Leu-D-Ala-NHOH, Ac-Arg-Cys-Gly-Val-Pro-Asp-$NH_2$, rhuman TIMP1; rhuman TIMP2, and phosphoramidon; cell adhesion molecules, including integrin agonists and antagonists including .alpha.v.beta.3 MoAb LM 609 and echistatin; anti-chemotactic agents including F-Met-Leu-Phe receptors, IL-8 receptors, MCP-1 receptors and MIP1-I/RANTES receptors; intracellular signaling inhibitors, including (a) protein kinase inhibitors, including both (i) protein kinase C (PKC) inhibitors (isozyme) including calphostin C, G-6203 and GF 109203 and (ii) protein tyrosine kinase inhibitors, (b) modulators of intracellular protein tyrosine phosphatases (PTPases) and (c) inhibitors of SH2 domains (src Homology$_2$ domains).

For some applications, it may be beneficial to administer the C3b inhibitory agents of the present invention in combination with a spasm inhibitory agent. For example, for urogenital applications, it may be beneficial to include at least one smooth muscle spasm inhibitory agent and/or at least one anti-inflammation agent, and for vascular procedures, it may be useful to include at least one vasospasm inhibitor and/or at least one anti-inflammation agent and/or at least one anti-restenosis agent. Suitable examples of spasm inhibitory agents include serotonin.sub.2 receptor subtype antagonists; tachykinin receptor antagonists; nitric oxide donors; ATP-seusltive potassium channel openers; calcium channel antagonists; and endothelin receptor antagonists.

Pharmacetical Carriers and Delivery Vehicles

In general, the C3b inhibitory agent compositions of the present invention, combined with any other selected therapeutic agents, are suitably contained in a pharmaceutically acceptable carrier. The carrier is non-toxic, biocompatible and is selected so as not to detrimentally affect the biological activity of the C3b inhibitory agent (and any other therapeutic agents combined therewith). The anti-C3b antibodies and inhibitory peptides useful in the invention may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, normal or lactated Ringer's solutions physiological phosphate-buffered saline. Hank's solution, dextrose solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, but are not limited to, microspheres, nanospheres or nanoparticles composed of proteins, liposomes, microparticles, carbohydrates, synthetic organic compounds, inorganic compounds, polymeric or copolymeric hydrogels and polymeric micelles.

For intra-articular delivery, the C3b inhibitory agent may be carried in above-described injectable liquid or gel carriers, above-described sustained-release delivery vehicles that are injectable, or a hyaluronic acid or hyaluronic acid derivative. For oral administration of non-peptidergic agents, the C3b inhibitory agent may be carried in an inert filler or diluent such as sucrose, cornstarch, or cellulose. For topical administration, the C3b inhibitory agent may be carried in spray, ointment, lotion, suppository, cream, gel, drop, liquid or powder, or in gel or microcapsular delivery systems via a transdermal patch. Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively. For intrathecal (IT) or intracerebroventricular (ICV) delivery, appropriately sterile delivery systems (e.g., liquids; gels, suspensions, etc.) can be used to administer the present invention. The compositions of the present invention may also include biocompatible exeipients, such as dispersing or wetting agents, emulsifiers, diluents, buffers, suspending agents, penetration enhancers, binders, thickeners, or flavoring agents (for oral administration).

Pharmaceutical Carriers for Antibodies and Peptides

More specifically with respect to anti-C3b antibodies and inhibitory peptides, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH-buffering substances and the like can be present in compositions comprising anti-C3b antibodies and inhibitory peptides. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-C3 or anti-C3b antibodies and inhibitory peptides can also be administered in the form of a depot injection or implant preparation that can be formulated in such a manner as to permit a sustained or pulsatile release of the active agents.

Pharmaceutically Acceptable Carriers for Expression Inhibitors

More specifically with respect to expression inhibitors useful in the methods of the invention, compositions are provided that comprise an expression inhibitor as described above and a pharmaceutically acceptable carrier or diluent. The composition may further comprise a colloidal dispersion system. Pharmaceutical compositions that include expression inhibitors may include, but are not limited to, solutions, emulsions, and liposome-containing formulations. These compositions may be generated from a variety of components that include, but are not limited to, preformed liquids, self-emulsifying solids, and self-emulsifying semisolids. The preparation of such compositions typically involves combining the expression inhibitor with one or more of the following: buffers, antioxidants, low molecular weight polypeptides, proteins, amino acids, carbohydrates including glucose, sucrose, or dextrins, chelating agents such as EDTA, glutathione and other stabilizers and excipients. Neutral buffered saline or saline mixed with non-specific serum albumin are examples of suitable diluents.

In some embodiments, the compositions may be prepared and formulated as emulsions, which are typically heterogeneous systems of one liquid dispersed in another in the form of droplets (see, Idson, in Pharmaceutical Dosage Forms, Vol. 1, Rieger and Banker (eds.), Marcek Dekker, Inc., N.Y., 1988). Examples of naturally occurring emulsifiers used in emulsion formulations include acacia, beeswax, lanolin, lecithin, and phosphatides. In one embodiment, compositions including nucleic acids can be formulated as microemulsions. A microemulsion, as used herein refers to a system of water; oil and amphiphile, which is a single optically isotropic and thermodynamically stable liquid solution (see Rosoff in Pharmaceutical Dosage Forms, Vol. 1). The method of the invention may also use liposomes for the transfer and delivery of antisense oligonucleotides to the desired site. Pharmaceutical compositions and formulations of expression inhibitors for topical administration may include transdermal patches, ointments, lotions, creams, gels, drops, suppositories, sprays, liquids, and powders. Conventional pharmaceutical carriers, as well as aqueous, powder or oily bases and thickeners and the like may be used.

Pharmaceutical Compositions and Delivery Methods Dosing

In another aspect, the invention provides compositions for inhibiting the adverse effects of C3b-dependent complement activation comprising a therapeutically effective amount of a C3b inhibitory agent and a pharmaceutically acceptable carrier. The C3b inhibitory agents can be administered to a subject in need thereof, at therapeutically effective doses to treat or ameliorate conditions associated with C3b-dependent complement activation. A therapeutically effective dose refers to the amount of the C3b inhibitory agent sufficient to result in amelioration of symptoms of the condition.

Therapeutic efficacy of C3b inhibitory compositions, appropriate dosages, and methods of the present invention in a given subject, can be determined in accordance with complement assays well known to those skill in the art. Complement generates numerous specific products. During the last decade, sensitive and specific assays have been developed and are available commercially for most of these activation products, including the small activation fragments C3a, C4a, and C5a and the large activation fragments Bb and sC5b-9. Most of these assays utilize monoclonal antibodies that react with new antigens (neoantigens) exposed on the fragment, but not on the native proteins from which they are formed, making these assays very simple and specific. ELISA technology is relied on mostly, although radioimmunoassay is still sometimes used for C3a and C5a. These latter assays measure both the unprocessed fragments and their 'desArg' fragments, which are the major forms found in the circulation. Unprocessed fragments and C5a desarg are rapidly cleared by binding to cell surface receptors and are hence present in very low concentrations, whereas C3a deArg does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. The classical pathway generates C4a, measurement of which should provide information about the activity of C3b inhibitor whether such an inhibitor is activating the classical pathway.

Modes of Administration

The pharmaceutical compositions comprising C3b inhibitory agents may be administered in a number of ways depending on whether a local or systemic mode of administration is most appropriate for the condition being treated. Additionally, as described herein above with respect to extracorporeal reperfusion procedures, C3b inhibitory agents can be administered via introduction of the compositions of the present invention to re-circulate blood or plasma. Further, the compositions of the present invention can be delivered by coating or incorporating the compositions on or into an implantable medical device.

Systemic Delivery

As used herein, the terms "systemic delivery" and "systemic administration" are intended to include, but are not limited to oral and parenteral routes. This includes intramuscular (IM), subcutaneous, intravenous (IV), intra-arterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous, and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

C3b inhibitory antibodies and polypeptides can be delivered into a subject in need thereof by any suitable means. Methods of delivery of C3b antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, C3b inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L.; Lee, V. H. L.) For example, STDHF is a synthetic derivative of fusidic acid, a steroidal surfactant that is similar in structure to the bile salts, and has been used as a permeation enhancer for nasal delivery.

The C3b inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life. Many polymer systems have been reported for protein delivery (Bae, Y. H., et al.; Hori, R., et al.; Yamakawa, I., et al.; Yoshihiro, I., et al.; Asano, M., et al.; Rosenblatt, J., et al.; Makino, K. J.; Takakura, Y., et al.)

Recently, liposomes have been developed with improved serum stability and circulation half-times. Furthermore, various methods of liposome and liposome-like preparations as potential drug carriers have been reviewed (see, e.g., U.S. Pat. No. 5,567,434; U.S. Pat. No. 5,552,157). The C3b inhibitory antibodies and polypeptides may be combined with other suitable ingredients, such as carriers and/or adjuvants for transdermal applications. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The C3b inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the C3b inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects as well as provide more control of the delivery timing and concentration of the active agents at the site of local delivery. Local administration provides a known concentration at the target site, regardless of inter patient variability in metabolism, blood flow, etc. Improved dosage control is also provided by the direct mode of delivery.

Local delivery of a C3b inhibitory agent may be achieved in the context of surgical methods for treating a disease or condition, such as for example during procedures such as arterial bypass surgery, atherectomy, laser procedures, ultrasonic procedures, balloon angioplasty and stent placement. For example, a C3b inhibitor can be administered to a subject in conjunction with a balloon angioplasty procedure, which involves inserting a catheter having a deflated balloon into an artery. The deflated balloon is positioned in proximity to the atherosclerotic plaque and is inflated such that the plaque is compressed against the vascular wall. As a result, the balloon surface is in contact with the layer of vascular endothelial cells on the surface of the blood vessel. The C3b inhibitory agent may be attached to the balloon angioplasty catheter in a manner that permits release of the agent at the site of the atherosclerotic plaque. The agent may be attached to the balloon catheter in accordance with standard procedures known in the art. For example, the agent may be stored in a compartment of the balloon catheter until the balloon is inflated, at which point it is released into the local environment. Alternatively, the agent may be impregnated on the balloon surface, such that it contacts the cells of the arterial wail as the balloon is inflated. The agent may also be delivered in a perforated balloon catheter such as those disclosed in Flugelman, M. Y., et al. See also published PCT Application WO 95/23161 for an exemplary procedure for attaching a therapeutic protein to a balloon angioplasty catheter. Likewise, the C3b inhibitory agent may be included in a gel or polymeric coating, applied to a stent, or incorporated into the material of the stent such that the stent elutes the C3b inhibitory agent after vascular placement. C3b inhibitory compositions used in the treatment of arthritides and other musculoskeletal disorders may be locally delivered by intra-articular injection. Such compositions may suitably include a sustained release delivery vehicle. As a further example of instances in which local delivery may be desired, C3b inhibitory compositions used in the treatment of urogenital conditions may be suitably instilled intravesically or within another urogenital structure.

Coatings on a Medical Device

C3b inhibitory agents such as antibodies and inhibitory peptides may be immobilized onto (or within) a surface of an implantable or attachable medical device. The modified surface will typically be in contact with living tissue after implantation into an animal body. By "implantable or attachable medical device" is intended any device that is implanted into, or attached to, tissue of an animal body, during the normal operation of the device for example stents and implantable drug delivery devices. Such implantable or attachable medical devices can be made from, for example, dextran, nitrocellulose, polystyrene, glass, diazocellulose, polyvinylchloride, polypropylene, polyethylene, sepharose, agar, starch, nylon, stainless steel, titanium, and biodegradable or biocompatible polymers.

Linkage of the protein to a device can be accomplished by any technique that does not destroy the biological activity of the linked protein, for example by attaching one or both of the N— C-terminal residues of the protein to the device. Attachment may also be made at one or more internal sites in the protein. Multiple attachments, both internal and at the ends of the protein, may be used. A surface of an implantable or attachable medical device can be modified to include functional groups for protein immobilization thereto, for example carboxyl, amide, amino, ether, hydroxyl, cyano, nitrido, sulfanamido, acetylinic, epoxide, silanic, anhydric, succinimic, azido. Coupling chemistries include, but are not limited to, the formation of esters, ethers, amides, azido and sulfanamido derivatives, cyanate and other linkages to the functional groups available on C3b antibodies or inhibitory peptides. C3b antibodies or inhibitory fragments can also be attached non-covalently by the addition of an affinity tag sequence to the protein, such as GST, polyhistidines, or biotin. Such affinity tags may be used for the reversible attachment of the protein to a device.

Treatment Regimens

In prophylactic applications, the pharmaceutical compositions are administered to a subject susceptible to, or otherwise at risk of, a condition associated with C3b-dependent complement activation in an amount sufficient to eliminate or reduce the risk of developing symptoms of the condition. In therapeutic applications, the pharmaceutical compositions are administered to a subject suspected of, or already suffering from, a condition associated with C3b-dependent complement activation in a therapeutically effective amount sufficient to relieve, or at least partially reduce, the symptoms of the condition. In both prophylactic and therapeutic regimens, compositions comprising C3b inhibitory agents may be administered in several dosages until a sufficient therapeutic outcome has been achieved in the subject. Application of the C3b inhibitory compositions of the present invention may be carried out by a single administration of the composition, or a limited sequence of administrations, for treatment of an acute condition, e.g., reperfusion injury or other traumatic injury. Alternatively, the composition may be administered at periodic intervals over an extended period for treatment of chronic conditions, such as arthritis or psoriasis.

EXAMPLES

The examples that follow are presented to describe embodiments and utilities of the invention and are not meant to limit the invention unless otherwise stated in the claims appended hereto. The description is intended as a non-limiting illustration, since many variations will become apparent to those skilled in the art in view thereof. It is intended that all such variation within the scope and spirit of the appended claims be embraced thereby. Changes can be made in the composition, operation, and arrangement of the method of the present invention described herein without departing from the concept and scope of the invention as defined in the claims.

Example 1

Production of Polyclonal Antibodies

This example describes a method of producing polyclonal antibodies against C3b. Polyclonal anti-human C3b antiserum is produced by immunizing rabbits with the C3b. Six-week old Rabbits, primed with BCG (bacillus Calmette-Guerin vaccine) are immunized by injecting 100 μg of C3b at 100 μg/ml in sterile saline solution. Injections are done every 4 weeks, with antibody titer monitored by ELISA assay. Culture supernatants are collected for antibody purification by protein A affinity chromatography.

Example 2

Production of Murine Monoclonal Antibodies

This example describes a method for producing murine monoclonal antibodies against rat or human C3b protein and/or polypeptides. Male A/J mice (Harlan, Houston, Tex.), 8-12 weeks old, are injected subcutaneously with 100 μg human or rat rC3b or rC3bA polypeptides in complete Freund's adjuvant (Difco Laboratories, Detroit, Mich.) in 200 μl of phosphate buffered saline (PBS) pH 7.4. At two-week intervals, the mice are twice injected subcutaneously with 50 μg of human or rat rC3b or rC3bA polypeptide in incomplete Freund's adjuvant. On the fourth week the mice are injected with 50 μg of human of rat rC3b or rC3bA polypeptide in PBS and are fused 4 days later. For each fusion, single cell suspensions are prepared from the spleen of an immunized mouse and used for fusion with Sp2/0 myeloma cells. $5 \times 10^8$ of the Sp2/0 and $5 \times 10^8$ spleen cells are fused in a medium containing 50% polyethylene glycol (M.W. 1450) (Kodak, Rochester, N.Y.) and 5% dimethylsulfoxide (Sigma Chemical Co., St. Louis, Mo.). The cells are then adjusted to a concentration of $1.5 \times 10^5$ spleen cells per 200 μl of the suspension in Iscove medium (Gibco, Grand Island, N.Y.), supplemented with 10% fetal bovine serum. Two hundred microliters of the cell suspension are added to each well of about twenty 96-well microculture plates. After about ten days culture supernatants are withdrawn for screening for reactivity with purified factor C3b in an ELISA assay. In the ELISA Assay: Wells of Immulon 2 (Dynatech Laboratories, Chantilly, Va.) microtest plates are coated by adding 50 υl of purified hC3b at 50 υg/ml or rat rC3b (or rC3bA) overnight at room temperature. The low concentration of C3b for coating enables the selection of high-affinity antibodies. After the coating solution is removed by flicking the plate, 200 μl of 1% BSA in PBS is added to each well for one hour to block the non-specific sites. An hour later, the wells are then washed with a buffer PBS. Fifty microliters of culture supernatants from each fusion well is collected, mixed with 50 ul 1% BSA in PBS, and then added to the individual wells of the microtest plates. After one hour of incubation, the wells are washed with PBS. The bound murine antibodies are then detected by reaction with horseradish peroxidase (HRP) conjugated goat anti-mouse IgG (Fc specific) (Jackson ImmunoResearch Laboratories, West Grove, Pa.) and diluted at 1:2,000 in blocking solution. TMB (tetra-methyl-benzidine solution) is added to the wells for color development for 15-20 minutes. The reaction is terminated by addition of 50 υl of 1M Ortho Phosphoric acid per well. The Optical Density at 450 nm of the reaction mixture is read with a Spectramax ELISA Reader (SPECTRA MAX 250, Molecular Devices, Sunnyvale, Calif.).

Example 3

Selection of Anti-C3b Monoclonal Antibodies

Culture supernatants from hybridoma cultures that test positive in the C3b binding ELISA assay described above can be tested in a binding assay to determine the binding affinity the C3b inhibitory agents may have for C3b. Polystyrene microtiter plate wells (96-well medium binding plates, Corning Costar, Cambridge, Mass.) are coated with C3b (20 ng/100 μl/well, Advanced Research Technology, San Diego, Calif.) in phosphate-buffered saline (PBS) pH 7.4 overnight at 4° C. After aspirating the C3b solution, wells are blocked with PBS containing 1% bovine serum albumin (BSA; Sigma Chemical) for 2 h at room temperature. Wells without C3b coating serve as the background controls. Allquots of hybridoma supernatants or purified anti-C3b MoAbs, at varying concentrations in blocking solution, are added to the wells. Following a 1 h incubation at room temperature, the wells are extensively rinsed with PBS. C3b-bound anti-C3b MoAb is detected by the addition of peroxidase-conjugated goat anti-mouse IgG (Sigma Chemical) in blocking solution, which is allowed to incubate for 1 h at room temperature. The plate is rinsed again thoroughly with PBS, and 100 υl of 3,3',5,5'-tetramethyl benzidine (TMB) substrate (Kirkegaard and Perry Laboratories, Gaithersburg, Md.) is added. The reaction of TMB is quenched by the addition of 100 υl of 1M phosphoric acid, and the plate is read at 450 nm in a microplate reader (SPECTRA MAX 250, Molecular Devices, Sunnyvale, Calif.).

The culture supernatants from the positive wells are then tested for the ability to inhibit complement activation in a functional assay such as the rabbit erythrocyte hemolysis assay. The cells in positive wells are then cloned by limiting dilution. The MoAbs are tested again for reactivity with hC3b in an ELISA assay as described above. The selected hybridomas are grown in spinner flasks and the spent culture supernatant collected for antibody purification by protein A affinity chromatography.

Example 4

Production of Humanized Anti-C3b Antibodies

This example describes the generation and production of humanized murine anti-C3b antibodies and antibody fragments. A murine anti-C3b monoclonal antibody is generated in Male A/J mice as per procedures well known in the art. The murine antibody is then humanized to reduce its immunogenicity by replacing the murine constant regions with their human counterparts to generate a chimeric IgG and Fab fragment of the antibody, which is useful for inhibiting the adverse effects of C3b-dependent complement activation in human subjects in accordance with the present invention.

Example 5

Tubing Loop as a Testing Model

This example describes the use of a tubing loop as a model for testing C3b inhibitory agents useful to prevent tissue damage resulting from extra corporeal circulation (ECC) such as a cardiopulmonary bypass (CPB) circuit. As discussed above, patients undergoing ECC during CPB suffer a systemic inflammatory reaction, which is partly caused by exposure of blood to the artificial surfaces of the extracorporeal circuit, but also by surface-independent factors like surgical trauma and ischemia-reperfusion injury (Butler, J., et al.; Edmunds, L. H.; Asimakopoulos, G.). It has further been shown that the alternative complement pathway plays a predominant role in complement activation in CPB circuits, resulting from the interaction of blood with the artificial surfaces of the CPB circuits (see Kirklin et al., 1983, 1986). Therefore, based on the observations described herein that C3b plays an essential role in both classical and alternative pathways, the tubing loop model is useful to screen for C3b inhibitory agents that are effective for use as therapeutic agents to prevent or treat an extracorporeal exposure-triggered inflammatory reaction with respect to alternative pathway complement activation.

A modification of a previously described tubing loop model for cardiopulmonary bypass circuits is utilized (see Gong et al., J Clinical Immunol. 16(4):222-229 (1996)) as described in Gupta-Bansal et al., Molecular Immunol. 37:191-201 (2000). Briefly, blood is freshly collected from a healthy subject in a 7 ml vacutainer tube (containing 7 units of heparin per ml of whole blood). Polyethylene tubing similar to what is used during CPB procedures (e.g., I.D. 2.92 mm; O.D. 3.73 mm, length: 45 cm) is filled with 1 ml of blood and closed into a loop with a short piece of silicone tubing. A control tubing containing heparinized blood with 10 mM EDTA is included in the study as a background control. Sample and control tubings are rotated vertically in a water bath for 1 hour at 37° C. After incubation, the blood samples are transferred into 1.7 ml microfuge tubes containing EDTA, resulting in a final concentration of 20 mM EDTA. The samples are centrifuged and the plasma is collected. C3b inhibitory agents, such as anti-C3b antibodies, are added to the heparinized blood immediately before rotation. The plasma samples are then subjected to assays to measure the concentration C3a and soluble C5b-9 as described in Gupta-Bansal et al., 2000.

For complement inhibition studies, various concentrations (100-600 nM) of the blocking anti-C3b monoclonal antibody described is added to the heparinized blood immediately before circulation for 1 hour at 37° C. After circulation/rotation in a 37° C. water bath for 1 hour, aliquots are analyzed for soluble C3a, C5a, and sMAC as described in ELISA assay kits (Quidel).

Using this simplified CPB paradigm in which standard CPB tubing is partially filled with fresh human blood, leaving an air-blood interface and where the tubing is joined end-to-end with a silicon sleeve to form a loop, such that this blood-filled loop is rotated in a heated water bath (37° C.) to simulate the movement of blood through a bypass circuit, there is marked activation of complement during the rotation of the blood in the tubing. Importantly, the blocking antihuman properdin antibody causes significant inhibition of this complement activation.

Example 6

Neutrophil Activation

This example describes an assay that measures neutrophil activation, which is useful as a measure of an effective dose of a C3b inhibitory agent for the treatment of conditions, associated with the complement activation in accordance with the methods of the invention. A method for measuring neutrophil elastase has been described in Gupta-Bansal, R., et al., Molecular Immunol. 37:191-201, 2000. Briefly, the complex of elastase and serum $\alpha_1$-antitrypsin is measured with a two-site sandwich assay that utilizes antibodies against both elastase and $\alpha_1$-antitrypsin. Polystyrene microtiter plates are coated with a 1:500 dilution of anti-human elastase antibody (The Binding Site, Birmingham, UK) in PBS overnight at 4° C. After aspirating the antibody solution, wells are blocked with PBS containing 1% BSA for 1 h at room temperature. Aliquots (100 µl) of plasma samples that are treated with or without a C3b inhibitory agent are added to the wells. Following a 2 h incubation at room temperature, the wells are extensively rinsed with PBS. Bound elastase-$\alpha_1$-anti-trypsin complex is detected by the addition of a 1:500 dilution of peroxidase conjugated-$\alpha_1$-antitrypsin antibody in blocking solution that is allowed to incubate for 1 h at room temperature. After washing the plate with PBS, 100 µl aliquots of TMB substrate are added. The reaction of TMB is quenched by the addition of 100 µl of phosphoric acid, and the plate is read at 450 nm in a microplate reader.

Anti-factor C3b-MoAbs can be prepared by standard methods well known in the art. For example, rodents (e.g. mice, rats, hamsters, and guinea pigs) can be immunized either with native C3 or C3b purified from human plasma or urine or with recombinant C3b or its fragments expressed by either eukaryotic or prokaryotic systems. Other animals can also be used for immunization, e.g. non-human primates, transgenic mice expressing human immunoglobulins, and severe combined immunodeficient mice transplanted with human B-lymphocytes. Hybridoma can be generated by conventional procedures well known in the art by fusing B lymphocytes from the immunized animals with myeloma cells (e.g., Sp2/0 and NS0). In addition, anti-factor C3b antibodies can be generated by screening of recombinant single-chain $F_v$ or $F_{ab}$ libraries from human B lymphocytes in phage-display systems. The specificity of the MoAbs to human C3b can be tested by enzyme linked immunosorbent assay (ELISA).

It would be evident to the one skilled in the art that in vitro studies of complement are representative of and predictive of the in vivo state of the complement system. By way of example, the use of in vitro ELISA (enzyme-linked immunosorbent assay) procedures to detect factor B associated with lipopolysaccharide (LPS) is a "simple, rapid and reliable method for the assessment of complement function particularly the detection of complement deficiency states". Thus, the in vitro technique can be used in vivo with the same likelihood of success in detecting alternative complement pathway activation in disease states. Furthermore, the standard rabbit erythrocyte hemolysis assay (described in Example 4), which assay is used to measure alternative complement pathway activity, is accepted in the art as being the "most convenient assay for the activity of the human alternative pathway".

The compounds of the present invention can be administered in the pure form, as a pharmaceutically acceptable salt derived from inorganic or organic acids and bases, or as a pharmaceutically 'prodrug.' The pharmaceutical composition may also contain physiologically tolerable diluents, carriers, adjuvants, and the like. The phrase "pharmaceutically acceptable" means those formulations, which are within the scope of sound medical judgment, suitable for use in contact with the tissues of humans and animals without undue toxicity, irritation, allergic response and the like, and are commensurate with a reasonable benefit/risk ratio. Pharmaceutically acceptable salts are well-known in the art, and are described by Berge et al. [14], incorporated herein by reference. Representative salts include, but are not limited to acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate(isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calcium, magnesium, aluminum, ammonium, tetramethyl ammonium, tetraethylammonium, methylammonium, dimethylammonium, trimethylammonium, triethylammonium, diethylammonium, and ethylammonium, and the like.

The pharmaceutical compositions of this invention can be administered to humans and other mammals enterally of parenterally in a solid, liquid, or vapor form. Enteral route includes oral, rectal, toipical, buccal, and vaginal administration. Parenteral route intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer.

The active compound is mixed under sterile conditions with a pharmaceutically acceptable carrier along with any needed preservatives, excipients, buffers, or propellants. Opthalmic formulations, eye ointments, powders and solutions are also contemplated as being within the scope of this invention. Actual dosage levels of the active ingredients in the pharmaceutical formulation can be varied to achieve the desired therapeutic response for a particular patient. The selected dosage level will depend upon the activity of the particular compound, the route of administration, the severity of the condition being treated, and prior medical history of the patient being treated. However, it is within the skill of the art to start doses of the compound at levels lower than required to achieve the desired therapeutic effect and to increase it gradually until optimal therapeutic effect is achieved. The total daily dose of the compounds of this invention administered to a human or lower animal may range from about 0.0001 to about 1000 mg/kg/day. For purposes of oral administration, doses that are more preferable can be in the range from about 0.001 to about 5 mg/kg/day. If desired, the effective daily dose can be divided into multiple doses for purposes of administration; consequently, single dose compositions may contain such amounts or submultiples thereof to make up the daily dose.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, as well as the duration of the treatment. The compounds of the present invention may also be administered in combination with other drugs if medically necessary.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include polyorthoesters and polyanhydrides. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions, which can be dissolved or dispersed in sterile water or other sterile injectable medium just prior to use.

Dosage forms for topical administration include powders, sprays, ointments and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a.) fillers or extenders such as starches, lactose, sucrose, glucose, mannitol and silicic acid, b.) binders such as carboxymethylcellulose, alginates, gelatin, polyvinylpyrrolidone, sucrose and acacia, c.) humectants such as glycerol, d.) disintegrating agents such as agar-agar, calcium carbonate, potato or tapioca starch, alginic acid, certain silicates and sodium carbonate, e.) solution retarding agents such as paraffin, f.) absorption accelerators such as quaternary ammonium compounds, g.) wetting agents such as cetyl alcohol and glycerol monostearate, h.) absorbents such as kaolin and bentonite clay and, i.) lubricants such as talc, calcium stearate, magnesium stearate, solid polyethylene glycols, sodium lauryl sulfate and mixtures thereof In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art. They may optionally contain opacifying agents and as well as be of a composition such that they release the active ingredient(s) only, or preferentially, in a certain part of the intestinal tract, optionally, in a delayed manner. Examples of embedding compositions, which can be used, include polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used such as, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The present invention also provides pharmaceutical compositions that comprise compounds of the present invention formulated together with one or more non-toxic pharmaceutically acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art, incorporated herein by reference.

The compounds of the present invention can also be administered to a patient in the form of pharmaceutlcally acceptable 'prodrugs.' The term "pharmaceutically acceptable prodrugs", represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided by Higuchi and Stella, incorporated herein by reference.

Example 7

Binding of Anti-C3b to C3b

Polystyrene microtiter plates were coated with human C3b (0.5 µg/50 µl per well) (Calbiochem, San Diego, Calif., Cat. No. 204860) in phosphate buffered saline (PBS) overnight at 4° C. After aspirating the C3b solution, wells were blocked with PBS containing 1% bovine serum albumin (BSA) (Sigma Chemical Company, St. Louis, Mo., Cat. No. A7888) for 1 hour at room temperature. Wells without C3b coating served as background controls. Aliquots of anti-C3b ((Quidel, San Diego, Calif., Catalog No. A205, Lot No. A205B22701) at varying concentrations in blocking solution were added to the wells. Following 1 hour incubation at room temperature, the wells were extensively rinsed with PBS.

C3b-bound anti-C3b monoclonal antibody was detected by the addition of goat anti-mouse IgG-peroxidase labeled at 1:2000 dilution in blocking solution, which was allowed to incubate for 1 hour at room temperature. After washing the plates with PBS, 100 µl of 3,3',5,5'-tetramethyl benzidine (TMB) substrate (Kirkegaard & Perry Laboratories, Gaithersburg, Md., Cat. No. A50-65-00) was added to each well. After incubation for 10 minutes at 25° C., the reaction of TMB was quenched by the addition of 100 µl of phosphoric acid, and the plate was read at 450 nm in a microplate reader (e.g., SPECTRA MAX 190, Molecular Devices, Sunnyvale, Calif.). The estimated $K_d$ of anti-C3b ((Quidel, San Diego, Calif., Catalog No. A205, Lot No. A205B22701) binding to C3b was based on the concentration of anti-C3b at 50% maximal binding (Microcal Origin Program).

Example 8

Alternative Pathway-Dependent MAC Assay

Since factor C3b is the critical component of the C3 convertase, it was of interest to us to determine whether the C3b antibody (Quidel, San Diego, Calif., Catalog No. A205, Lot No. A205B22701) might appreciably affect the terminal aspects of the alternative complement cascade by preventing the deposition of C5b-9. The final end product of this pathway is the C5b-9 membrane-attack complex (MAC). To analyze the effects of the C3b antibody on MAC formation via the alternative pathway, an assay was utilized in which bacterial LPS was used as a substrate to initiate the alternative complement pathway cascade.

Previous studies have demonstrated that lipopolysaccharide (LPS) from *Salmonella typhosa* (*S. Typhosa*) (Sigma Chemical Company, Cat. No. 6386) serves as a potent substrate for complement alternative pathway activation. Microtiter wells were coated with LPS (2 µg/50 µl per well) in PBS overnight at 4° C. Uncoated wells served as background controls. After aspirating the LPS solution, wells were treated with blocking solution and incubated with various concentrations of normal human serum. Following 2-hour incubation at 37° C., deposited MAC was detected with mouse anti-human soluble C5b-9 monoclonal antibody (Quidel, Cat. No. A239) using standard ELISA methodologies essentially as described in the Examples above. The effect of the blocking antibody on the MAC formation was evaluated by adding various concentrations of blocking antibody to a fixed concentration of serum (8% in blocking solution). The amount of inhibition of deposited C5b-9 was determined using the antibody detection system described in the Examples above.

Addition of increasing amounts of normal human serum, which contains all of the complement components, resulted in increased MAC deposition on the LPS surface. The formation of MAC in this assay could be completely prevented by the addition of the anti-C3c monoclonal antibody. These data indicate that C3b is in fact necessary for progression of the terminal complement cascade.

Example 9

Alternative Pathway-Dependent Hemolysis

To confirm and extend these results, the anti-C3b antibody (Quidel, San Diego, Calif., Catalog No. A205, Lot No. A205B22701) was examined in another assay of the alternative pathway. Rabbit erythrocytes initiate the alternative complement cascade, and the resulting formation of MAC causes lysis of these cells. If the aati-C3b antibody is capable of complete inhibition of the alternative pathway, then addition of the reagent to rabbit erythrocytes bathed in human serum should prevent cellular lysis. This can be assayed by examining the light scattering caused by intact red blood cells; lysed cells do not diffract light, and there is a consequent reduction in scattered light. It is well established that rabbit erythrocytes specifically activate the complement alternative pathway, with a resulting lysis of the cells by the C5b-9 complex. Normal human serum, at various concentrations in Gelatin Veronal Buffer (GVB) (Advanced Research Technology) with 5 mM $MgCl_2$ and 10 mM EGTA, was incubated at 37° C. with a fixed number of rabbit erythrocytes (Advanced Research Technology). A progressive decrease in light scatter (due to lysis of intact cells) was measured at 700 nm as a function of time in a temperature-controlled ELISA plate reader. To determine the ability of blocking antibody to inhibit hemolysis of rabbit erythrocytes, various concentrations of the blocking antibody were added to a fixed concentration of normal human serum (10%) and the assay was performed as described above. The data were recorded and analyzed with a SpectraMax plate reader and software.

Addition of serum in the absence of anti-C3c antibody resulted in lysis of the cells and a dramatic reduction in light scattering. Addition of increasing concentrations of the antibody caused a decrement in erythrocyte lysis, with x nM antibody completely blocking MAC-mediated cellular destruction. These results confirm that monoclonal antibodies that bind and block interactions sites on C3b are potent reagents that can completely abrogate the effects of the alternative complement pathway.

Example 10

Blocking Agents: Screening and Identification

Agents, which selectively block the formation of complement activation products via the classical or the alternative complement pathway, including preferred anti-human C3b antibodies, may be obtained and then screened, identified and selected as taught herein, for their ability to substantially or completely block the formation or production of alternative complement pathway-dependent activation products, including in conditions involving initiation of the classical complement pathway. A commercially available anti-human C3b monoclonal antibody (Quidel, San Diego, Calif., Catalog No. A205, Lot No. A205B22701) was evaluated for blocking activity in assays. The antibody inhibited complement dependent lysis of rRBC and C5b-9 formation.

According to the present invention, agents are therefore effectively screened for essentially complete, partial or no blocking activity in one or more assays as described herein. Including blocking of factor B binding to properdin-bound C3b, inhibition of C3 convertase formation, blocking of alternative pathway-dependent C3a, C5a, and MAC formation, blocking of alternative pathway-dependent hemolysis, blocking of alternative pathway-dependent C3a formation, of blocking of one or more markers of alternative pathway-dependent cell activation, including markers of leukocyte activation (CD11b), platelet activation (e.g., P-selection, CD62P) and platelet-leukocyte adhesion. Agents may be further screened for lack of activation of Fc gamma receptors and/or classical pathway activation.

Having described the invention, the following is claimed:

1. A method of inhibiting C3b dependent complement activation in blood of a subject in need thereof, comprising:
    administering to blood of the subject an amount of an anti-C3b monoclonal antibody or antigen-binding fragment thereof effective to inhibit C3b dependent complement activation and hemolysis in the subject.

2. The method of claim 1 wherein the anti-C3b monoclonal antibody or antigen-binding fragment thereof specifically binds to C3b protein sequences involved in C3b binding to properdin or factor B or C3b cleavage from C3.

3. The method of claim 1 wherein the antibody or fragment thereof is a recombinant antibody.

4. The method of claim 1 wherein the antibody has reduced effector function.

5. The method of claim 1 wherein the antibody is a chimeric, humanized or human antibody.

6. The method of claim 1 wherein the antibody is produced in a C3 deficient transgenic animal.

7. A method of treating adverse effects of C3b-dependent complement activation in a subject suffering from ischemia-reperfusion injury, comprising:
 administering to blood of the subject an amount of an anti-C3b monoclonal antibody or antigen-binding fragment thereof effective to inhibit C3b-dependent complement activation in the subject.

8. The method of claim 7, wherein the ischemia-reperfusion injury is associated with at least one of aortic aneurysm repair, cardiopulmonary bypass, vascular reanastomosis in connection with organ transplants and/or extremity/digit replantation, stroke, myocardial infarction, and hemodynamic resuscitation following shock and/or surgical procedures.

* * * * *